(12) United States Patent
Frost et al.

(10) Patent No.: US 12,115,095 B2
(45) Date of Patent: *Oct. 15, 2024

(54) ORTHOPEDIC DEVICE

(71) Applicant: Ossur Iceland ehf, Reykjavik (IS)

(72) Inventors: Lindsay Frost, Foothill Ranch, CA (US); Jared Olivo, Foothill Ranch, CA (US); Harry Duane Romo, Foothill Ranch, CA (US)

(73) Assignee: Ossur Iceland ehf, Reykjavik (IS)

( * ) Notice: Subject to any disclaimer, the term of this patent is extended or adjusted under 35 U.S.C. 154(b) by 533 days.

This patent is subject to a terminal disclaimer.

(21) Appl. No.: 17/379,137

(22) Filed: Jul. 19, 2021

(65) Prior Publication Data

US 2021/0346186 A1     Nov. 11, 2021

Related U.S. Application Data

(63) Continuation of application No. 15/478,478, filed on Apr. 4, 2017, now Pat. No. 10,617,549.

(60) Provisional application No. 62/418,867, filed on Nov. 8, 2016, provisional application No. 62/317,737, filed on Apr. 4, 2016.

(51) Int. Cl.
*A61F 5/01*      (2006.01)
*A61F 5/05*      (2006.01)

(52) U.S. Cl.
CPC .......... *A61F 5/0123* (2013.01); *A61F 5/0118* (2013.01); *A61F 5/0125* (2013.01); *A61F 5/013* (2013.01); *A61F 5/05* (2013.01); *A61F 5/0106* (2013.01); *A61F 2005/0158* (2013.01); *A61F 2005/0165* (2013.01); *A61F 2005/0167* (2013.01); *A61F 2005/0169* (2013.01); *A61F 2005/0172* (2013.01); *A61F 2005/0179* (2013.01); *A61F 2005/0197* (2013.01)

(58) Field of Classification Search
CPC .... A61F 5/0106; A61F 5/0118; A61F 5/0123; A61F 5/0125; A61F 5/013
See application file for complete search history.

(56) References Cited

U.S. PATENT DOCUMENTS 2,172,484  A     9/1939   Tessier
4,041,940  A     8/1977   Frankel et al.
(Continued)

FOREIGN PATENT DOCUMENTS

EP     1086672 A2     3/2001
EP     1475060 B1     4/2006
(Continued)

OTHER PUBLICATIONS

"AP037 Heavy Duty D-Ring," American Plastics, requested from www.americanplastics.com/catalog.asp?cat=47982163&p=1&c=4>, 2017, 1 Page.
(Continued)

*Primary Examiner* — Keri J Nelson
(74) *Attorney, Agent, or Firm* — Workman Nydegger

(57) ABSTRACT

An orthopedic device, first and second struts, and a range-of-motion limiting pivot assembly connecting to the first and second struts. The pivoting assembly having an engagement member linked to a tab disposed and arranged for pulling radially outward away from a central axis of the pivoting assembly for adjusting the range of motion of the pivoting assembly.

18 Claims, 22 Drawing Sheets

(56) References Cited

U.S. PATENT DOCUMENTS

| | | | |
|---|---|---|---|
| 4,171,555 A | 10/1979 | Bakker et al. |
| 4,271,999 A | 6/1981 | Stravitz |
| 4,299,014 A | 11/1981 | Wood |
| 4,337,764 A | 7/1982 | Lerman |
| 4,361,142 A | 11/1982 | Lewis et al. |
| 4,381,768 A | 5/1983 | Erichsen et al. |
| 4,610,056 A | 9/1986 | Emmert |
| 4,628,916 A | 12/1986 | Lerman et al. |
| 4,702,975 A | 10/1987 | Fields |
| 4,708,130 A | 11/1987 | Grudem |
| 4,768,500 A | 9/1988 | Mason et al. |
| 4,776,326 A | 10/1988 | Young et al. |
| 4,817,588 A | 4/1989 | Bledsoe |
| 4,844,057 A | 7/1989 | Hoy |
| D308,186 S | 5/1990 | Udelhofen et al. |
| 5,000,169 A | 3/1991 | Swicegood et al. |
| 5,009,223 A | 4/1991 | Defonce |
| 5,018,514 A | 5/1991 | Grood et al. |
| 5,133,341 A | 7/1992 | Singer et al. |
| 5,135,469 A | 8/1992 | Castillo |
| 5,244,455 A | 9/1993 | Swicegood et al. |
| 5,256,135 A | 10/1993 | Avihod |
| 5,267,946 A | 12/1993 | Singer et al. |
| D344,610 S | 2/1994 | Keller |
| 5,302,169 A | 4/1994 | Taylor |
| 5,316,547 A | 5/1994 | Gildersleeve |
| 5,372,572 A | 12/1994 | Tamagni |
| D357,435 S | 4/1995 | Cook |
| 5,421,810 A | 6/1995 | Davis et al. |
| 5,425,700 A | 6/1995 | Aaserude et al. |
| 5,437,619 A | 8/1995 | Malewicz et al. |
| 5,460,599 A | 10/1995 | Davis et al. |
| D364,126 S | 11/1995 | Ochiai et al. |
| 5,628,069 A | 5/1997 | Ebert |
| 5,814,000 A | 9/1998 | Kilbey |
| D399,172 S | 10/1998 | Anscher |
| 5,827,208 A | 10/1998 | Mason et al. |
| 6,004,283 A | 12/1999 | Young |
| D426,791 S | 6/2000 | Nezu |
| D427,547 S | 7/2000 | Yoshiguchi |
| 6,110,138 A | 8/2000 | Shirley |
| D435,807 S | 1/2001 | Anscher |
| 6,383,156 B1 | 5/2002 | Enzerink et al. |
| 6,461,318 B2 | 10/2002 | Freeman et al. |
| 6,689,080 B2 | 2/2004 | Castillo |
| 6,821,261 B2 | 11/2004 | Doty et al. |
| 6,960,177 B2 | 11/2005 | Turrini et al. |
| 6,969,364 B2 | 11/2005 | Sterling |
| 7,018,351 B1 | 3/2006 | Iglesias et al. |
| 7,037,287 B2 | 5/2006 | Cormier et al. |
| 7,097,627 B2 | 8/2006 | Enzerink et al. |
| D529,180 S | 9/2006 | Ingimundarson et al. |
| D530,426 S | 10/2006 | Muehlenberend |
| D530,820 S | 10/2006 | Muehlenberend |
| 7,128,723 B2 | 10/2006 | Doty et al. |
| 7,201,728 B2 | 4/2007 | Sterling |
| 7,235,059 B2 | 6/2007 | Mason et al. |
| D546,955 S | 7/2007 | Bauerfiend et al. |
| D563,270 S | 3/2008 | Zeng |
| 7,384,406 B2 | 6/2008 | Enzerink et al. |
| D577,828 S | 9/2008 | Ingimundarson et al. |
| 7,485,103 B2 | 2/2009 | Mason et al. |
| 7,513,881 B1 | 4/2009 | Grim et al. |
| 7,597,674 B2 | 10/2009 | Hu et al. |
| D610,946 S | 3/2010 | Harada |
| 7,722,555 B2 | 5/2010 | Doty et al. |
| D619,497 S | 7/2010 | Paik |
| D619,498 S | 7/2010 | Paik |
| D619,726 S | 7/2010 | Win |
| D623,760 S | 9/2010 | Chiang |
| D625,654 S | 10/2010 | Spater |
| 7,833,181 B2 | 11/2010 | Cormier et al. |
| 7,867,183 B2 | 1/2011 | Kazmierczak et al. |
| D631,787 S | 2/2011 | Grimm et al. |
| 7,905,851 B1 | 3/2011 | Bledsoe |
| 7,918,809 B2 | 4/2011 | Enzerink et al. |
| D637,942 S | 5/2011 | Lee et al. |
| 7,963,933 B2 | 6/2011 | Nace |
| 7,967,765 B2 | 6/2011 | Nathanson |
| 8,021,317 B2 | 9/2011 | Arnold et al. |
| D647,819 S | 11/2011 | Kolasa |
| D656,430 S | 3/2012 | Spater |
| 8,172,781 B2 | 5/2012 | Oddou et al. |
| 8,216,166 B2 | 7/2012 | Einarsson et al. |
| 8,273,045 B2 | 9/2012 | Ceriani |
| 8,277,403 B2 | 10/2012 | Ceriani et al. |
| D673,880 S | 1/2013 | Boothby et al. |
| D673,994 S | 1/2013 | Geller |
| D675,249 S | 1/2013 | Giroux |
| 8,425,439 B1 | 4/2013 | McKeon et al. |
| 8,517,965 B2 | 8/2013 | Doty et al. |
| D693,930 S | 11/2013 | Manalo |
| 8,585,623 B2 | 11/2013 | Ingimundarson |
| 8,591,444 B2 | 11/2013 | Bejarano et al. |
| D702,151 S | 4/2014 | Kaneko et al. |
| 8,690,812 B2 | 4/2014 | Moir et al. |
| 8,728,018 B2 | 5/2014 | McCune |
| 8,821,426 B2 * | 9/2014 | Einarsson ............. A61F 5/0106 602/26 |
| 8,864,692 B2 | 10/2014 | Ingimundarson et al. |
| D726,925 S | 4/2015 | Fraser et al. |
| D735,872 S | 8/2015 | Ljubimir et al. |
| D739,303 S | 9/2015 | Kinskey |
| 9,125,730 B2 | 9/2015 | Ingimundarson et al. |
| D748,013 S | 1/2016 | Spater |
| 9,233,018 B2 | 1/2016 | Chetlapalli |
| D749,227 S | 2/2016 | Takama |
| 9,480,591 B2 | 11/2016 | Chen |
| D775,514 S | 1/2017 | Muhlenkamp, IV et al. |
| D782,364 S | 3/2017 | Nykoluk |
| D787,076 S | 5/2017 | Siddiqui et al. |
| 10,617,549 B2 * | 4/2020 | Frost ........................ A61F 5/05 |
| 2002/0183672 A1 | 12/2002 | Enzerink et al. |
| 2003/0155389 A1 | 8/2003 | Swartzentruber |
| 2004/0068215 A1 | 4/2004 | Adelson et al. |
| 2005/0070831 A1 | 3/2005 | Cormier et al. |
| 2005/0086772 A1 | 4/2005 | Yoshiguchi |
| 2005/0089772 A1 | 4/2005 | Kawaguchi et al. |
| 2005/0148917 A1 | 7/2005 | Nathanson |
| 2006/0036045 A1 | 2/2006 | Wilson et al. |
| 2006/0155229 A1 | 7/2006 | Ceriani et al. |
| 2006/0155230 A1 | 7/2006 | Mason et al. |
| 2006/0155232 A1 | 7/2006 | Ceriani |
| 2006/0206045 A1 | 9/2006 | Townsend et al. |
| 2006/0247565 A1 | 11/2006 | Cormier et al. |
| 2007/0038168 A1 | 2/2007 | Turrini et al. |
| 2007/0213648 A1 | 9/2007 | Ferrigolo et al. |
| 2008/0092271 A1 | 4/2008 | Victor |
| 2009/0182254 A1 | 7/2009 | Cho |
| 2009/0216165 A1 | 8/2009 | Christenhusz et al. |
| 2010/0256543 A1 | 10/2010 | McCune |
| 2011/0009786 A1 | 1/2011 | Chan |
| 2011/0082402 A1 | 4/2011 | Oddou et al. |
| 2011/0178448 A1 | 7/2011 | Einarsson |
| 2013/0253396 A1 | 9/2013 | Chetlapalli |
| 2013/0269629 A1 | 10/2013 | Holt, Jr. |
| 2014/0018828 A1 | 1/2014 | Foerster et al. |
| 2014/0364782 A1 | 12/2014 | Knecht |
| 2015/0018735 A1 | 1/2015 | Chetlapalli et al. |
| 2015/0025435 A1 | 1/2015 | Sherman |
| 2015/0057586 A1 | 2/2015 | Glace et al. |
| 2015/0100005 A1 | 4/2015 | Lu |
| 2015/0100006 A1 | 4/2015 | Lu |
| 2015/0141888 A1 | 5/2015 | Chiang et al. |
| 2015/0296929 A1 | 10/2015 | Kung |
| 2015/0318636 A1 | 11/2015 | Lappoehn |
| 2016/0089258 A1 | 3/2016 | Chen |

FOREIGN PATENT DOCUMENTS

| | | |
|---|---|---|
| EP | 1475060 B2 | 9/2009 |
| WO | 9322992 A1 | 11/1993 |

(56) References Cited

FOREIGN PATENT DOCUMENTS

| WO | 0202035 A1 | 1/2002 |
|----|------------|--------|
| WO | 2005046536 A1 | 5/2005 |
| WO | 2015106317 A1 | 7/2015 |

OTHER PUBLICATIONS

"Beastee Dee," Tri-Poinr, requested from www.tri-point.com/products/plastic-buckles/d-rings-and-strap-attachments/peastee-dee/>, 2017, 2 Pages.
"DDR Black Plastic Double D Ring," National Webbing, requested from www.nationalwebbing.com/products/DDR-Black-Plastic-Double-D-Ring.html>, 2017, 2 Pages.
"SNDR Black Plastic Snap D Ring," National Webbing, requested from www.nationalwebbing.com/products/SNDR-Black-Plastic-Snap-D-Ring.html>, 2017, 2 Pages.
"#TR1.38 Triangle Rings for 38mm Straps Nickel, Gunmetal or Light Gold," SewCreativeSupplies, requested from www.sewcreativesupplies.com.au/t138-triangle-glides-for-38mm-webbing-nickel-gunmetal-or-light-gold>, 2017, 2 Pages.
International Search Report From PCT Application No. PCT/US2017/025851, Aug. 17, 2017.
International Search Report and Written Opinion from PCT Application No. PCT/US2013/032951, May 29, 2013.
"Gll Rehab Alternatives", Products Engineered for Better People Performance, at least of May 9, 2003. 2 Pages.
"Rehab Alternatives", The Gll Rehab Solutions, at least of May 9, 2003. 2 Pages.
"GII Rehab", GII Orthotics Europe, at least of May 9, 2003. 2 Pages.
Notice of Opposition to European Patent Application No. 04101985. 2, Apr. 5, 2006, 12 Pages.
"T Scope Premier Post-Op Knee Brace", Breg Inc, 4 Pages, 2017.

\* cited by examiner

ORTHOPEDIC DEVICE

CROSS-REFERENCE TO RELATED APPLICATIONS

This application is a continuation of U.S. application Ser. No. 15/478,478, filed Apr. 4, 2017, which claims the benefit of U.S. Provisional Patent Application No. 62/317,737, filed on Apr. 4, 2016, and U.S. Provisional Patent Application No. 62/418,867, filed on Nov. 8, 2016, which are incorporated by reference herein in their entirety for all purposes.

FIELD OF THE DISCLOSURE

The disclosure relates to orthopedic devices, including immobilization braces, such as knee and elbow braces to aid user outcomes following surgery or injury.

BACKGROUND

In orthopedic devices, and more particularly adjustable knee or elbow braces or supports, it is desirable that the brace can limit the range of motion of a lower limb relative to the upper limb both as to bending in flexion, and in extension of the lower limb relative to the upper limb. Various immobilization brace arrangements have been proposed, and these have included, such as for the knee, upper struts for extending along the thigh, and lower struts for extending along the lower leg or calf. These braces or supports are often arranged in a "double upright" configuration because they are provided both on the inside or medial side of the leg, and on the outer or lateral side of the leg. The medial and lateral struts are normally padded, and provided with straps to hold them in place by circumferential tension. Pivoting arrangements are provided for coupling the upper and lower struts, and stops are provided for limiting extension and flexion of the knee.

Common indications for immobilization of the knee include anterior-, posterior-, medial-, and lateral-collateral ligament repairs and injuries, meniscal repairs, tibial plateau fractures, patellar tendon repairs, osteochondral repairs, condylar fractures, and sprains or strains of the knee. Common indications for immobilization of the elbow include fracture stabilization of the elbow, distal humerus, proximal radius or ulna, muscle, tendon and ligament repairs, reconstructions or injuries, range of motion control of the elbow post injury, and elbow hypertension.

Many prior art immobilization braces have shortcomings because they tend to be unduly bulky, have complicated adjustment mechanisms, cause undue discomfort to the limbs, or are not ergonomically configured. These prior art braces also may not hold proper or desired configuration during use, and can often inadvertently adjust to a position or configuration not desired or intended.

Donning and doffing of prior art braces can be a laborious and tedious procedure, particularly in the instance of an elbow brace whereby the user has only one good arm to don and doff the brace. Prior art braces may require extensive tightening and positioning of various components during donning of the brace, which can necessitate similar work during doffing of the brace. The difficulties in donning and doffing may lead to improper positioning and securing of prior art braces.

Other difficulties arise in properly fitting an orthopedic brace in a consistent manner, particularly when the orthopedic brace must be consistently donned and doffed by the user. Frequent adjustments made to straps and other components of the brace can make it difficult for a user to adjust the brace to a fit properly snug while not being overly tight. It may be difficult for a user or a clinician tasked with fitting a brace to gauge the required amount that a strap should be tightened. Even if a strap has been set to a desired length/tightness, the act of setting the strap may make later donning and doffing more difficult, as it can become challenging to buckle or clip a strap having no slack.

Many prior art orthopedic braces have drawbacks that limit the durability and/or comfort of the braces. Typically, an orthopedic brace includes padding intended to cushion the portions of the body to which the brace is worn. However, such padding is often attached using hook and loop fasteners, and is often built or positioned in a manner that leads to detachment of the padding from the brace or migration of the padding from the intended position on the brace, requiring frequent replacement or repositioning of the padding, and limiting the overall comfort of the brace. The amount of hook and loop fastener components included in such braces often leads to the inadvertent sticking or tangling of straps, and can make organizing the straps and other components of the brace more difficult during donning, doffing, or storage of the brace.

There is need for an orthopedic brace that can be comfortably fit to a user while providing easy adjustment and intuitive flexion and extension settings and other settings, with reduced or eliminated inadvertent adjustment of such settings. There is need for an orthopedic brace that provides easy donning and doffing while enabling a consistently appropriate, comfortable and snug fit. There is need for an orthopedic brace that provides benefits without being overly bulky or uncomfortable to a user, and that provides effective padding while maintaining durability and ease of use.

SUMMARY

The embodiments of the disclosure relate to orthopedic braces and supports that overcome the drawbacks in the prior art.

According to an embodiment, an orthopedic device includes a pivot assembly coupling a first strut and a second strut. The pivot assembly may include a first plate disposed within a cover, such that the first plate has a plurality of engagement surfaces disposed along an outer periphery of the first plate, an arcuate channel defined by an inner peripheral surface of the cover and the first plate, and a first pivot stop having a carriage slidably disposed within the arcuate channel and having an engagement member. The engagement member may be slidably disposed within the carriage, and coupled to a tab disposed radially outward from the carriage. The carriage biases the engagement member radially inward relative to the carriage to engage against an engagement surface of the first plate to lock rotation of the first pivot stop. Radially outward movement of the tab disengages the engagement member from the engagement surface to unlock rotation of the first pivot stop.

In another embodiment, the orthopedic device may include an upright assembly having a strap attachment member and a clasp coupling member. A strap is attached to the strap attachment member and extends therefrom. The strap includes a clasp assembly configured to couple to the clasp coupling member. The clasp assembly includes a fastener portion having an opening configured to couple with a corresponding coupling member. A handle portion is joined to the fastener portion at a first hinge, and is rotatable relative to the fastener portion about the first hinge. The handle portion includes a clip that enables detachable coupling of the handle portion to the fastener portion, and a strap attachment portion is coupled to the handle portion at a second hinge. The strap attachment portion is rotatable relative to the handle portion about the second hinge, and has a strap attachment member. The clasp assembly is moveable between an open configuration and a closed configuration. The opening and the strap attachment portion may be spaced apart at a greater distance in the open configuration than in the closed configuration.

In yet another embodiment, the orthopedic device may include an upright assembly having a strut including an adjustment aperture configured with a plurality of wider sections spaced apart by narrower sections, and a paddle having an interior channel configured to receive the strut. The paddle may include a lever extending parallel to the interior channel. A post may extend from the lever into the interior channel toward a post opening on a side of the paddle opposite the lever. The post can be biased into the interior channel by the lever, such that the paddle is adjustably coupled to the strut. The post preferably extends through a wider section of the adjustment aperture to lock a position of the paddle. A depression of the post toward the lever frees the post from the adjustment aperture to enable translation of the paddle relative to the strut.

The embodiments offer an intuitive arrangement that allows for the orthopedic device to be easy to apply. The orthopedic device has brackets and straps that make the device simple for donning, and indicia or other means to educate a user on what may be adjusted, and a preferred sequence for securing the device. The composition and arrangement of the orthopedic device features enable a lightweight brace that offers protection to avoid inadvertent tampering of settings, and is comfortable to wear. The orthopedic device has improved fitting arrangements over prior art devices due in part to paddle assemblies that are more anatomically contoured and simply adjustable for both height and circumferential sizing yet with secure locking features, and in combination with the straps enables quick and easy opening and adjustment of the orthopedic device while offering a lower profile over prior art devices.

These and other features, aspects, and advantages of the present disclosure will become better understood regarding the following description, appended claims, and accompanying drawings.

Figure 1:
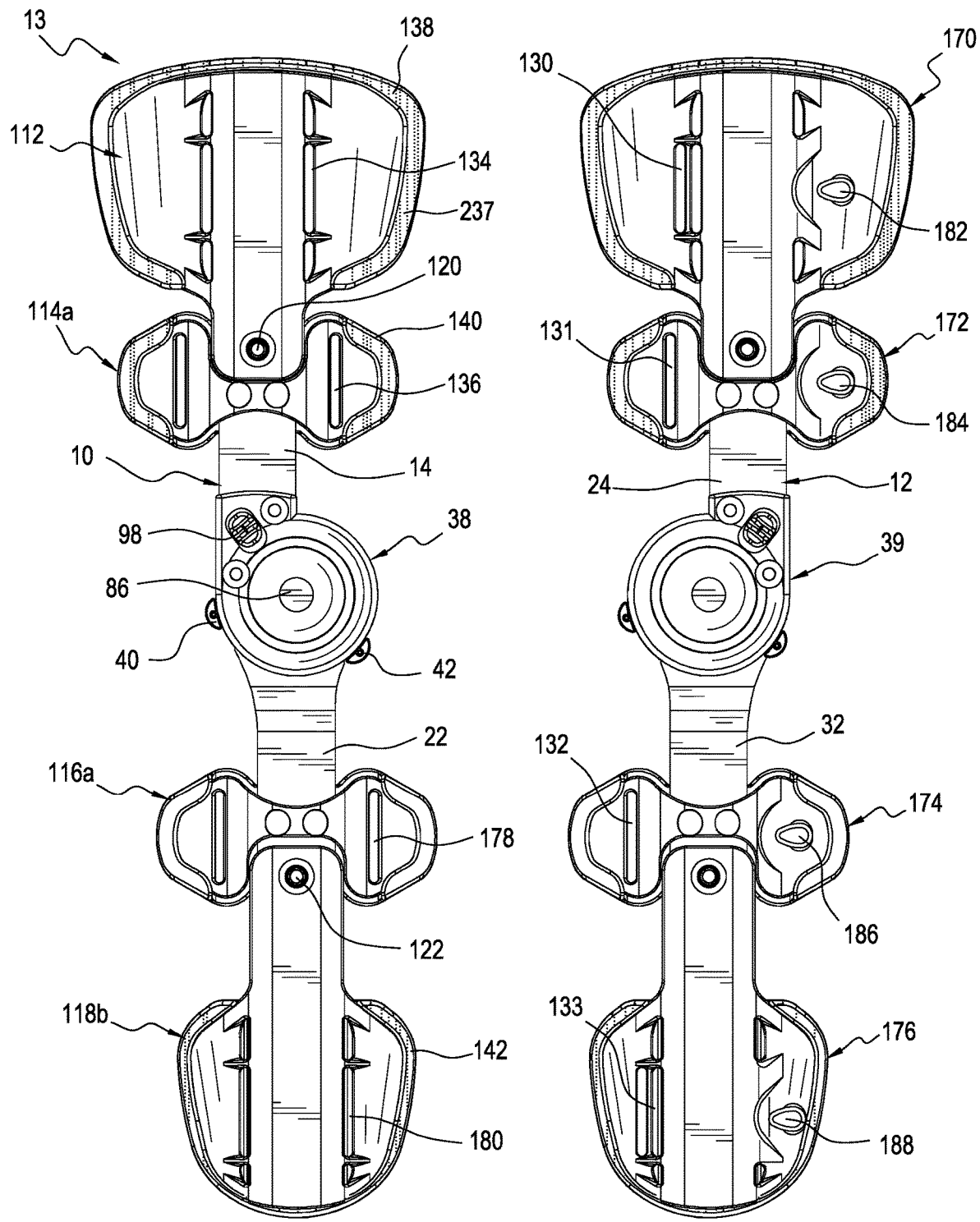
FIG. 1 is an elevational view of first and second upright assemblies of an orthopedic device in an immobilization or post-operative knee brace.

The drawings are not necessarily drawn to scale, but instead are drawn to provide a better understanding of the components, and are not intended to be limiting in scope, but to provide exemplary illustrations.

DETAILED DESCRIPTION OF VARIOUS EMBODIMENTS

For further ease of understanding the exemplary embodiments of an orthopedic device in an immobilization or post-operative knee or elbow brace as disclosed, these terms may be used with the features of the exemplary embodiments. The term "upper" refers to a location that is top or above a median portion (such as in a pivoting assembly proximate to the knee). Likewise, the term "lower" refers to a location below a median portion (such as in a pivoting assembly proximate to the knee) and is in contrast to the term "upper."

The terms "proximal" and "distal" are used referring to relative locations of parts or places on the limbs. Proximal then refers to something closer to the torso while distal refers to parts and places away from the torso. The femur is proximal to the knee, which is proximal to the ankle, which is proximal to the toes.

The terms "inner" or "inside" also have their ordinary meaning and refer to an inside portion or location adjacent to or more proximate to a leg or knee. The terms "outer" or "outside" have their ordinary meaning and refer to a relative location opposite an inner or inside portion, and is the side or surface typically on the outside of or proximate to the outside of the device.

The terms "medial" and "lateral" are relative terms understood as indicating location near the midsaggital plane or midline. Therefore, elements near the midline are "medial" and those elements further from the midline are considered "lateral." The term "central" is used to denote the area along the midline of a joint dividing and sharing regions of the medial and lateral regions. The medial side of the knee is the inside part or side nearest to the other knee, while the lateral side of the knee faces away from the center of the body and is farthest from the other knee.

The terms "rigid," "flexible," and "resilient" may distinguish characteristics of portions of certain features of the orthopedic brace. The term "rigid" should denote that an element of the device is generally devoid of flexibility. Within the context of support members that are "rigid," it should indicate that they do not lose their overall shape when force is applied, and they may break if bent with sufficient force. The term "flexible" should denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties that may have some degree of flexibility or resiliency.

It will be understood that usage of ordinals, such as "first," "second," and etc., are nominally used as associative denotations, but are not necessarily provided to denote spatial location. Rather, the ordinal merely associates one element with another element, or distinguishes one element from another element.

Various embodiments described herein are in the exemplary form of an immobilization or post-operative knee brace. However, it will be understood that similar embodiments and components as described, considered individually or in combination with other components, may be used for an orthopedic device in an elbow brace, ankle brace, shoulder brace, or other brace in which motion control and/or motion limiting of a body joint is desired. The components do not have to be used with the other components described herein.

FIG. 1 illustrates first and second upright assemblies 10 and 12, which may be positioned on opposite sides of a user's leg (medial and lateral) when a knee brace 13 is donned. The first upright assembly 10 includes an upper or first strut 14 and a lower or second strut 22 coupled to one another by a pivot assembly 38. Likewise, the second upright assembly 12 includes an upper or first strut 24 and a lower or second strut 32 coupled to one another by a pivot assembly 39. Such struts may sometimes be referenced as femoral or proximal struts (extending along the femur or upper leg bone), and tibial or distal struts (extending along the tibia or principal lower leg bone). Preferably, the struts 14, 22, 24, 32 are formed from a material (e.g., aluminum) that provides sufficient rigidity to support and brace the knee joint, while also being somewhat malleable to allow optional bending by a clinician for better conformation to a user's leg. When worn, however, the struts 14, 22, 24, 32 do not bend or yield to the user's leg, but remain stiff or rigid when worn by the user.

Various features and components of the first and second upright assemblies 10, 12 will now be described with specific reference to the first upright assembly 10. It will be understood, however, that the described features and components are also applicable to the second upright assembly 12. The pivot assembly 38 enables rotation of the upper strut 14 relative to the lower strut 22 about a central axis (shown here as surrounding central fastener 86). The pivot assembly 38 includes pivot stops 40 and 42, which are configurable to limit the relative rotation of the upper and lower struts 14, 22 to limit extension and flexion of a user's knee when the brace has been donned. For a post-operative user, it is often desirable to limit bending of the knee in the extension direction (straightening out the leg) and/or the flexion direction (bending the leg).

The exemplary pivot assembly 38 also includes a drop lock assembly as evidenced by a drop lock button 98 configured to quickly and easily lock the relative pivoting of the upper and lower struts 14, 22. When the drop lock button 98 is moved from an unlocked position to a locking position, the drop lock assembly 96 functions to lock the first upright assembly 10 so rotation of the upper and lower struts 14, 22 relative to one another is prevented. At least the drop lock assembly may be adapted from U.S. patent application publication no. 2013/0253396, published Sep. 26, 2013, and incorporated herein by reference.

Figure 2:
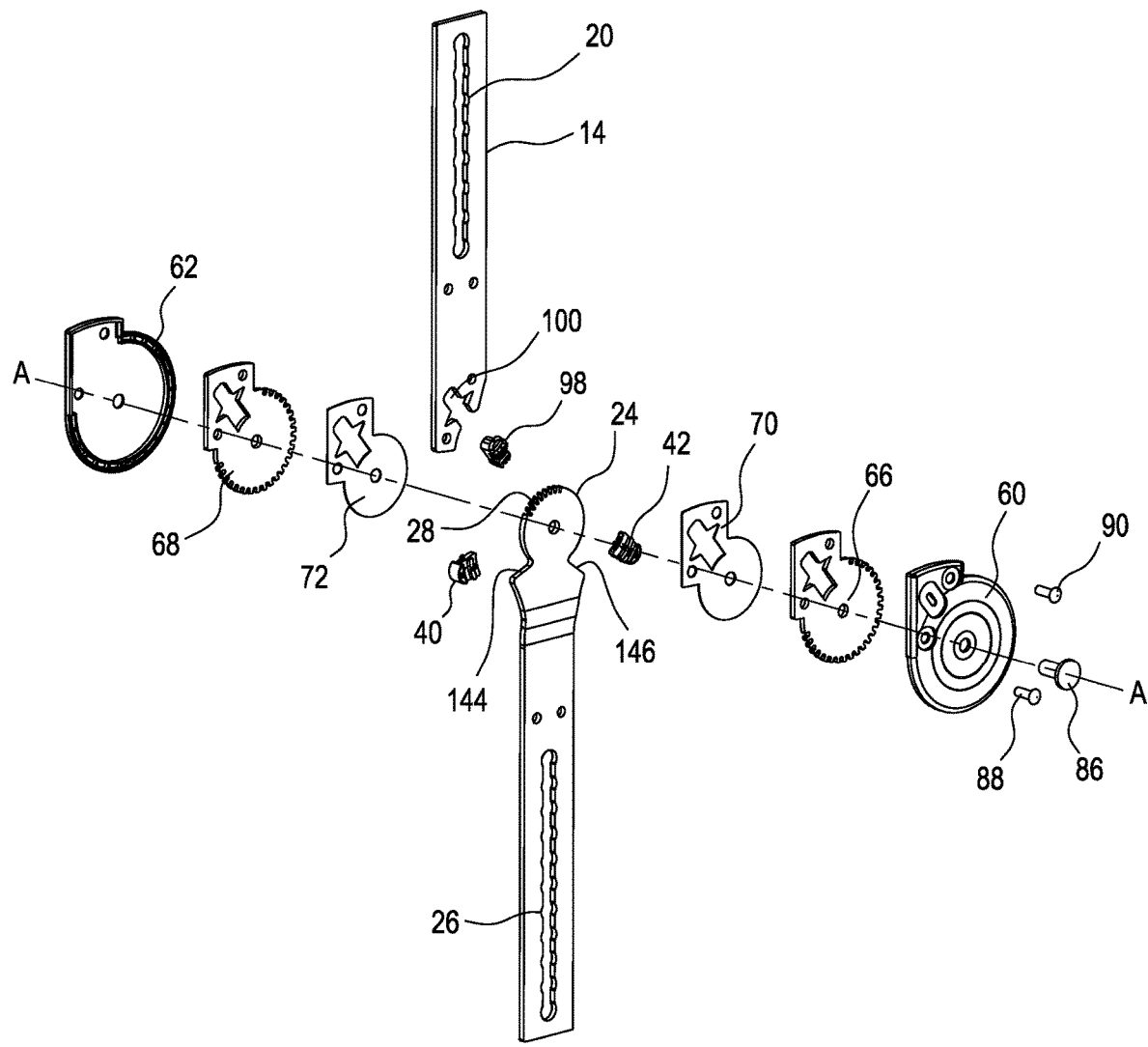
FIG. 2 is an exploded view of the first upright assembly of FIG. 1.

The first upright assembly 10 includes first and second upper paddle assemblies 112, 114a, and first and second lower paddle assemblies 118b, 116a. In the illustrated embodiment, the first upper paddle assembly 112 is adjustably mounted along the length of the upper strut 14, and the second lower paddle assembly 116a is adjustably mounted along the length of the lower strut 22 by respective locking mechanisms 120, 122. The upper strut 14 and lower strut 22 each include a respective adjustment aperture (as seen in FIG. 2) 20, 26, formed as a longitudinal slot having a plurality of relatively wide sections spaced apart by relatively narrow sections.

The locking mechanisms 120, 122 are operable with the adjustment apertures 20, 26 to enable the first upper paddle assembly 112 and first lower paddle assembly 118b to be adjustably locked to the respective upper and lower struts 14, 22. In the illustrated embodiment, the second upper paddle assembly 114a and second lower paddle assembly 116a are fixedly attached to the respective upper and lower struts 14, 22. In alternative embodiments, any of or combinations of the paddle assemblies 112, 114a, 116a, 118b may be configured as adjustable/translatable along the respective strut 14, 22.

The paddle assemblies 112, 114a, 116a, 118b of the first upright assembly 10 and the paddle assemblies 170, 172, 174, 176 of the second upright assembly 12 are configured to carry, support, and guide a number of straps to enable fitting of the brace upon a user. The illustrated embodiment includes integrally formed strap attachment members 130, 131, 132, 133 disposed on the second upright assembly 12 and configured to enable the attachment of straps, and strap guiding slots 134, 136, 178, 180 disposed on the first upright assembly 10 configured to receive and guide the straps. The illustrated embodiment also includes integrated clasp coupling members 182, 184, 186, 188 disposed on the second upright assembly 12 and configured to engage with a corresponding clasp to enable fastening of a strap to the respective paddle assembly.

A number of straps may be attached to the strap attachment members 130, 131, 132, 133 on the second upright assembly 12, passed through the strap guiding slots 134, 136, 178, 180 of the first upright assembly 10, then passed back around again to the second upright assembly 12 where clasped ends of the straps can be coupled to the clasp coupling members 182, 184, 186, 188 to form a completed strap circumference for each strap. Alternative embodiments may include different configurations of strap attachment members, strap guiding members, and/or clasp coupling members than the particular embodiment illustrated. Some embodiments may swap the relative locations of strap attachment members and strap guiding slots or may alternate positions of such components. In addition, some embodiments may include one or more buckles, integrated sections of hook fastener material (e.g., for attachment to corresponding loop fastener material), and/or other strap fastening means.

As shown, the clasp coupling members 182, 184, 186, 188 are integrally formed with their respective paddle assemblies 170, 172, 174, 176. This can beneficially provide a more secure attachment of straps to the paddle assemblies and can ensure that attached straps maintain a proper positional relationship to the paddle assemblies during the brace by a user of the brace. As opposed to a non-integrated buckle or other fastener attached to a paddle assembly with its own section of strap, the integrated clasp coupling members 182, 184, 186, 188 allow direct attachment of a strap to a paddle assembly, enabling the strap and paddle assembly to better maintain positional relationship and to avoid migration and slipping of one component relative to the other.

The paddle assemblies have a contoured and low profile to accommodate the shape of a leg. Beneficially, the large surface area and contoured shape of the paddle assemblies aid in the securing and fitting of a knee brace to a user's leg, and minimizes shifting of the leg within the brace. In addition, using a plurality of paddle assemblies aids in securing the brace components to a user's leg while simultaneously allowing for adjustable use and custom fitting.

The first upper paddle assembly 112 and first lower paddle assembly 118b may be adjusted to higher and lower positions relative to a user's knee aligned with the pivot assembly 38, while the second upper paddle assembly 114a and second lower paddle assembly 116a are maintained near the pivot assembly 38. In this manner, a brace can simultaneously support the upper and lower extremities of a user's leg, according to needed custom fitting parameters, while simultaneously maintaining support at constant and standard distances above and below the pivot assembly 38. This can advantageously allow for customizable fitting of the brace with no sacrifice to support near the knee joint itself.

As depicted, one or more of the paddle assemblies may include pads configured to reside between the paddle assemblies and the leg of a user when the brace is being worn. In the illustrated embodiment, the first upright assembly 10 includes pads 138, 140, and 142. Preferably, the pads are formed from a soft, elastomeric material such as natural rubber or one or more synthetic rubber materials (e.g., ethylene vinyl acetate ("EVA")). In a preferred embodiment, the peripheral edges of the pads extend about or past, or both, the peripheral edges of the paddle assemblies to minimize and protect from any sharp edges arising from the paddle assemblies, and therefore provide greater comfort to the user. For example, the pads may wrap about the edges of the paddle assemblies, or be oversized relative to the paddle assemblies, and may be contoured to correspond in shape to the paddle assemblies, as shown.

The pads 138, 140, and 142 are joined onto their respective paddle assemblies such that a portion of the pad extends from the inner surface of the paddle assembly around to the outer surface of the paddle assembly, as shown. Beneficially, this enables the pads 138, 140, 142 to be attached to the respective paddle assemblies with no additional hook and loop fastener materials or other fastening means. This minimizes the potential for the pads to become detached and/or to migrate or slip out of proper position relative to the paddle assemblies. In addition, the pad structure and attachment allow for a lower overall thickness/profile of the brace, as the need for additional hook and loop materials or other components between a pad and paddle assembly is reduced or eliminated. This reduces the bulk of the brace.

The illustrated embodiment omits pads at the second lower paddle assemblies 116a and 174. An optional anti-migration strap (not shown) may instead be positioned adjacent to the second lower paddle assemblies 116a, 174 on the inner surfaces of the second lower paddle assemblies 116a, 174. In some embodiments, an anti-migration strap is an integrated anti-migration strap integrally coupled to the device. The anti-migration strap may be configured to wrap around the circumference of the user's leg in combination with a corresponding strap, and the anti-migration strap may be attached to the corresponding strap (e.g., through hook and loop fastener material, buttons, and/or other suitable fasteners). The anti-migration strap functions to broaden the strap to urge uniform pressure about the circumference of the leg to limit migration. The anti-migration strap is preferably formed from a material that is flexible and breathable and that provides frictional properties, such as a high friction foam material. Preferably, the anti-migration strap is positioned so it may be wrapped around the widest portion of a user's calf to aid in preventing migration of the brace.

As depicted in FIG. 2, the pivot assembly 38 includes an outer or first cover 60, an outer or first plate 66, an outer or first bearing 70, a strut head 24 from which the lower strut 22 extends, an inner or second bearing 72, an inner or second plate 68, and an inner or second cover 62, all of which are positioned about a central axis A-A as connected by a central fastener 86. The first and second covers 60, 62, and first and second plates 66, 68 may define a flat, disc-like shape. The central fastener 86 extends through central holes of each component to attach the components of the pivot assembly 38 to the lower strut 22. Upper strut fasteners 88, 90 are used to fasten the components of the pivot assembly 38 to the upper strut 14. As shown, the first and second plates 66, 68 and the first and second bearings 70, 72 are rigidly secured to the upper strut 14, while the lower strut 22 is rotatable relative to the first and second plates 66, 68 and the first and second bearings 70, 72 about the central axis A-A.

While the first and second plates 66, 68, and first and second covers 60, 62 are depicted and described as being discretely separate elements, they may be formed monolithically. For example, the outer plate and outer cover may be formed together as a single element, to form a unitary element constructed from a same material or a combination of materials. The combination of the outer plate and outer cover, and the inner plate and inner cover, whether considered unitary or discretely separate, may be referred to as a pivoting element. For example, the combination of the outer plate and the outer cover may be referred to as an outer pivoting element, and the inner plate and the inner cover may be referred to as an inner pivoting element.

Pivot stops 40, 42 are rotatable relative to the first and second plates 66, 68. The pivot stops 40, 42 are configured to selectively be engaged with the notches of the first and second plates 66, 68 to delimit flexion and extension of the lower strut 22 relative to the upper strut 14 as the stop edges 144, 146 abut against the pivot stops 40, 42 to prevent further rotation of the lower strut 22 past the pivot stops 40, 42. The drop lock assembly as evidenced by drop lock button 98 is disposed within a drop lock recess 100 that extends through the first and second plates 66, 68, first and second bearings 70, 72, and the upper strut 14. The drop lock assembly 96 is configured to be selectively engaged with the notches 28 of the lower strut 22 to lock rotation of the upper and lower struts 14, 22 relative to one another.

The first and second bearings 70, 72 are preferably formed from a polymer material such as a polyamide (e.g., nylon) or polytetrafluoroethylene. As shown, the first and second bearings 70, 72 are positioned between the first and second plates 66, 68 and the strut head 24 of the lower strut 22. In this configuration, the first and second bearings 70, 72 can provide smooth rotation of the lower strut 22 relative to the upper strut 14. This beneficially provides a user with a more comfortable and natural feel during flexion and/or extension motions of the knee, by avoiding any catching or binding between the first and second plates 66, 68 and the strut head 24. In addition, the first and second bearings 70, 72 function to protect the adjacent components to which they are applied, increasing the durability and usability of the knee brace.

Figure 3:
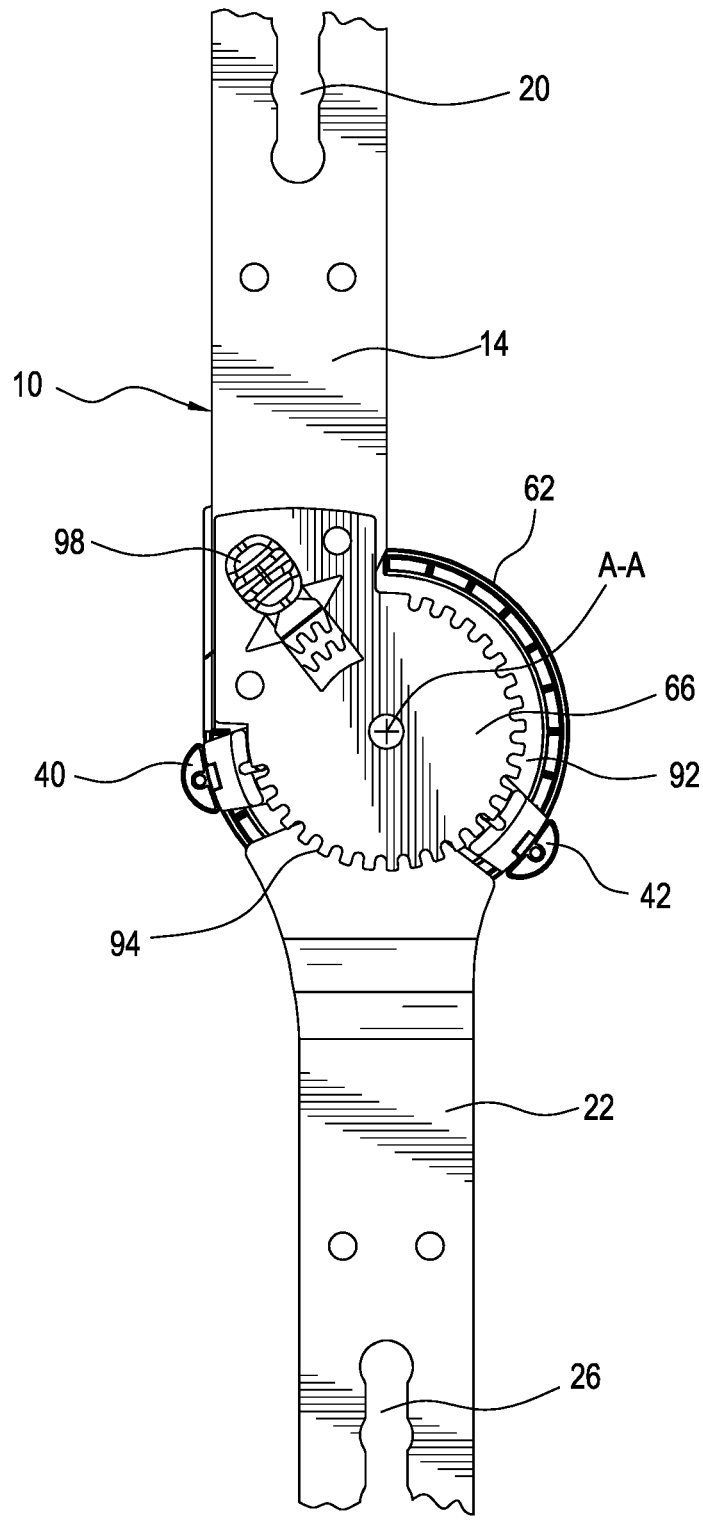
FIG. 3 is a partial elevational view of the first upright assembly of FIG. 1 without an outer cover provided thereon.
Figure 4:
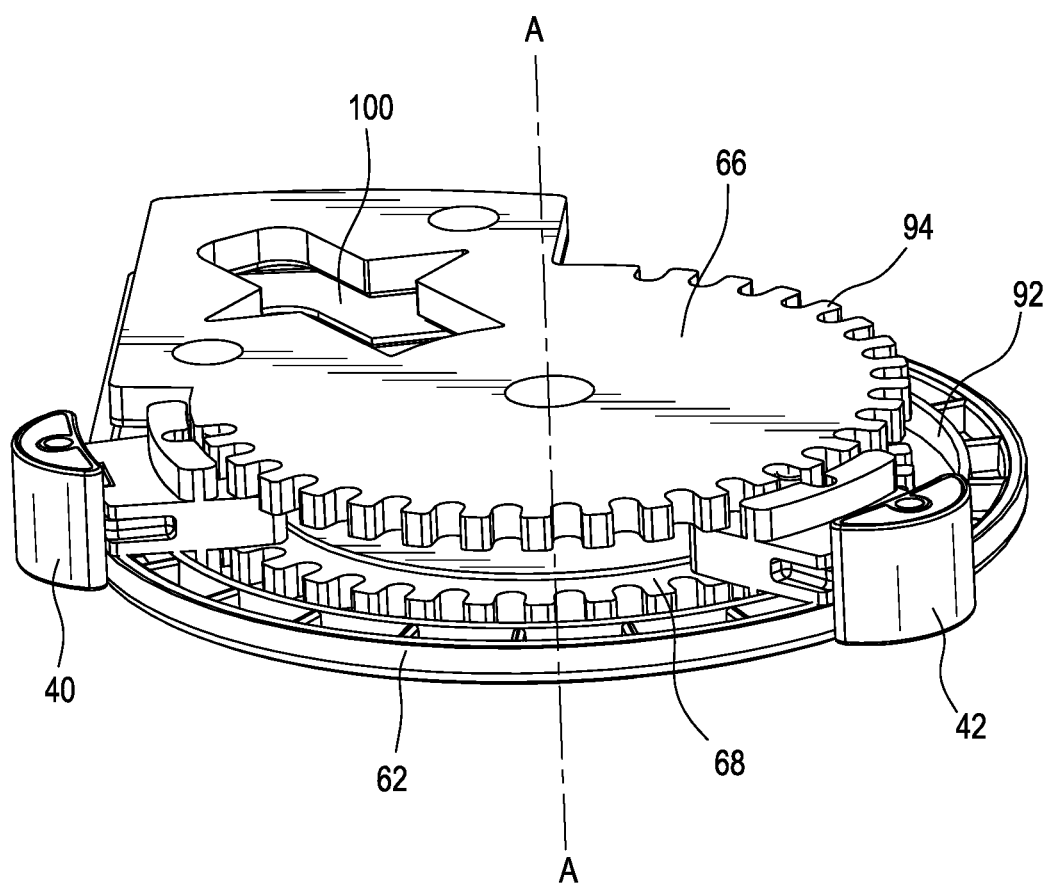
FIG. 4 is a perspective view of the first upright assembly of FIG. 1 showing the pivot assembly.

FIGS. 3 and 4 illustrate the pivot assembly 38 with the first cover 60 removed. The pivot stops 40, 42 are disposed within an arcuate channel 92 defined by the circumferential space between the first and second plates 66, 68 and the interior surface formed by the first and second covers 60 (shown above), 62. The first and second plates 66, 68 include engagement surfaces as shown by example in raised extensions 94 (defining notches therebetween) that are radially aligned so the pivot stops 40, 42 may be received by the notches of both first and second plates 66, 68. As shown, by configuring the raised extensions 94 to extend radially outward from the first and second plates 66, 68, the plates may be formed as substantially solid integrated pieces that can beneficially omit arcuate slots or arcuate cutout portions (e.g., are substantially solid other than fastening holes and a drop lock recess 100). The arcuate path through which the pivot stops 40, 42 rotate is disposed between the first and second plates 66, 68 and the first and second covers 60, 62, and need not be defined by structural cutouts through the surfaces of the first and second plates 66, 68 or other components of the pivot assembly 38.

Figure 5:
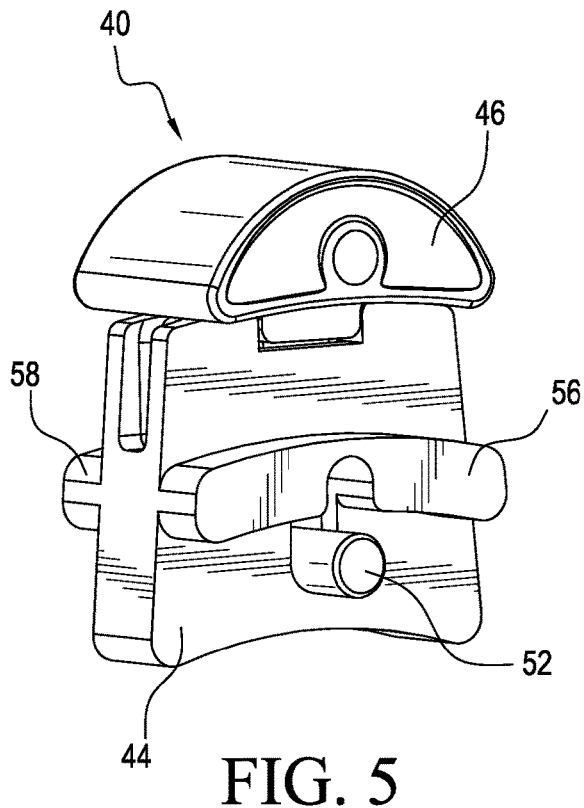
FIGS. 5-7 illustrate an exemplary embodiment of a pivot stop or range of motion (ROM) button configured to limit flexion and extension of the pivot assembly.
Figure 6:
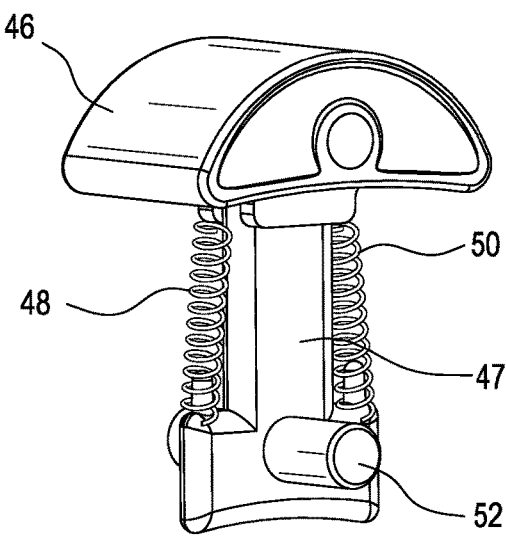
Figure 7:
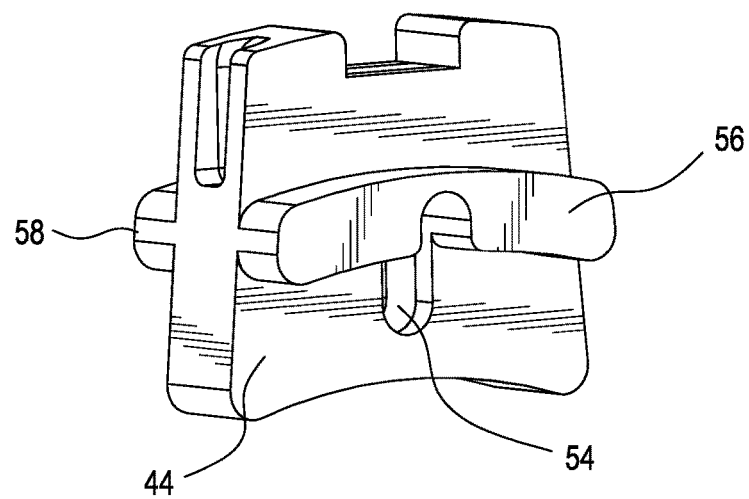

FIGS. 5-7 illustrate an exemplary embodiment of a pivot stop 40, which includes a carriage 44 and a tab 46 attached to a body 47 that slidably inserts into the carriage 44 and moves parallel or is axial with an axis of the carriage 44. The tab 46 is preferably configured in size, shape, and/or texture to allow a user to engage with the tab 46 by pulling the tab radially outward so the pivot stop 40 may be disengaged from the notches of the first and second plates 66, 68 and repositioned. An engagement member, such as a pin 52 is coupled to the body 47 and extends transversely through the body 47 to protrude through a pin slot 54 formed through the carriage 44 and configured to receive the pin 52. The pin 52 is configured to extend into the notches defined by the raised extensions 94 of the first and second plates 66, 68. Flanges 56, 58 also protrude from the carriage 44 and are configured to be received into the arcuate channel 92 to secure the carriage 44 within the arcuate channel 92.

Springs 48 and 50 are coupled to the body 47 and are configured to bias the body 47 and connected pin 52 downward (i.e., radially inward) relative to the carriage 44. In operation, when a user pulls upward (i.e., radially outward) on the tab 46, the body 47 is moved radially outward relative to carriage 44, which is held in place within the arcuate channel 92 by example in the form of flanges 56, 58 extending from the carriage. Outward movement of the body 47 moves the pin 52 to the outer section of the pin slot 54, disengaging the pin 52 from the notches of the plates 66, 68 and enabling a user to freely rotate the pivot stop 40 about the arcuate channel 92 to a desired position. Upon releasing the tab 46, the springs 48, 50 bias the body 47 downward/radially inward regarding the carriage 44, moving the pin 52 into the inner section of the pin slot 54 where the pin 52 engages with the notches of the first and second plates 66, 68 to lock the pivot stop 40 in position.

The described configuration beneficially allows for easy adjustment of the pivot stops 40, 42 when desired while simultaneously avoiding unintended adjustments made through accidental actuation of a pivot stop. The pull-out functionality of a pivot stop requires a very deliberate action to disengage and reposition the pivot stop. This allows for easy adjustment and, because a tab probably will not accidentally be pulled, protects against inadvertent adjustments. Configurations which rely on push-in functionality are easily actuated through normal use, accidental bumping, etc. Likewise, configurations that rely on actuation through push or pull movements perpendicular to the plane defined by the first and second plates 66, 68 and/or that rely on lever action are also susceptible to accidental disengagement avoided by the pull-out functionality of the pivot stops described herein.

Figure 8A:
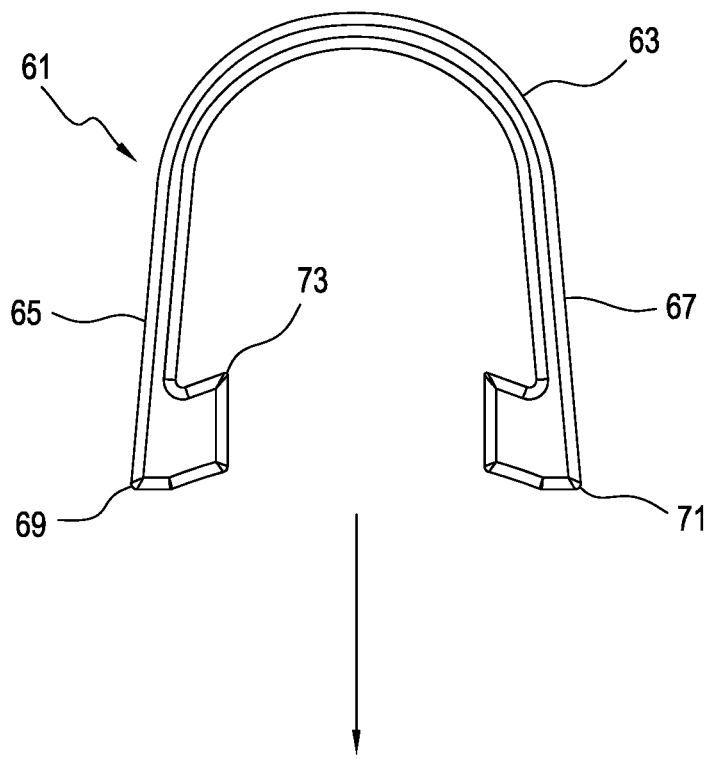
FIGS. 8A-8C illustrate a lock for another embodiment of the pivot assembly.
Figure 8B:
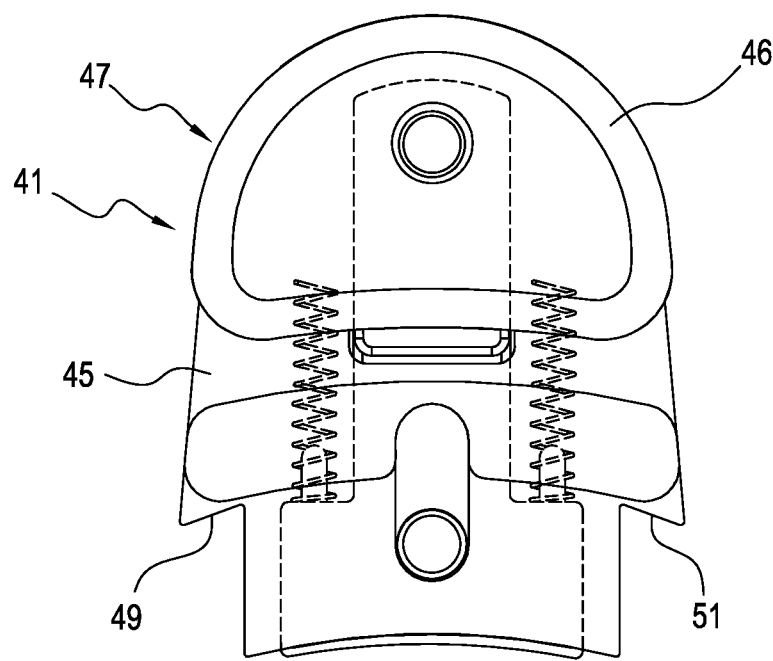
Figure 8C:
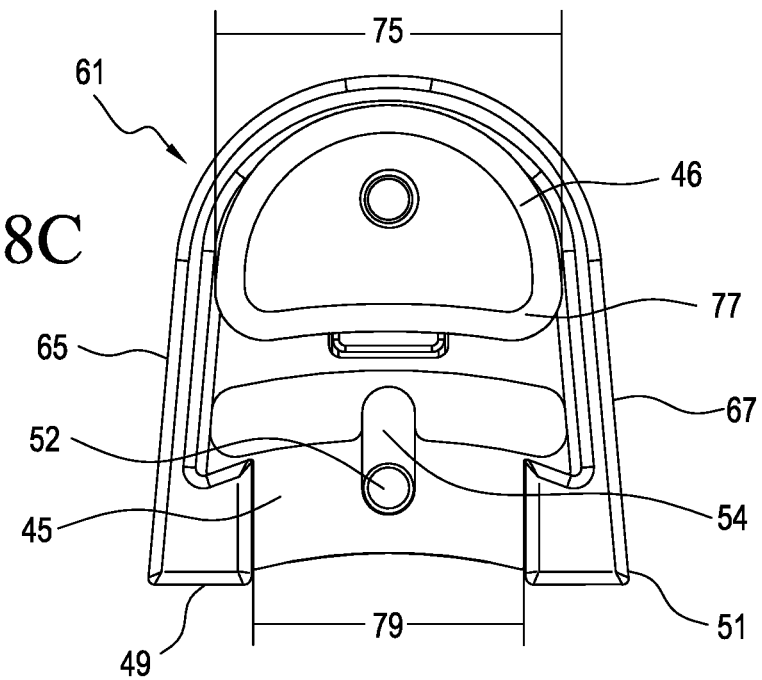

FIGS. 8A-8C exemplify another embodiment of a pivot stop or range of motion (ROM) button 41, which includes a range of motion (ROM) lock 61. The ROM lock 61 is arranged to lock the hinge at an angle set by the clinician. The locking by the ROM lock 61 has a two-fold purpose including (1) prevention of patient tampering of the set range of motion of the hinge, and (2) prevention of accidental bumping or unintentional movement of the pivot stops 40, 42 or ROM button 41. The lock can be applied to ROM buttons arranged for pushing in toward a central axis A-A of the hinge, or to ROM buttons arranged for pulling away from the central axis A-A of the hinge, and serves a similar purpose in both ROM hinge variations. In either configuration, whether pulling or pushing, the lock advantageously arrests the tab from further adjustment.

FIGS. 8A and 8B exemplify an embodiment of the ROM lock 61. The ROM lock 61 is fitted over the surface 53 of the tab 46 of the ROM button 41 and snaps to first and second flanges 49, 51 in a variation of the carriage 45 that sets the angle in the hinge. As shown, the ROM lock 61 may define a generally U-shape profile having a center portion 63, and first and second arms 65, 67 extending therefrom. The first and second arms 65, 67 terminate with first and second latches 69, 71 arranged to engage the first and second flanges 49, 51 of the carriage 45.

FIG. 8C exemplifies dimensions to the ROM lock 61 whereby an inside width 79 between the first and second arms 65, 67 of the ROM lock 61 is smaller than a width 75 of the tab 46. When the ROM lock 61 is pushed over a surface 53 of the tab 46, the first and second arms 65, 67 deflect from the surface 53. This creates a spring force with the ROM lock 61, which results in the first and second latches 69, 71 (shown above) snapping against the first and second flanges 49, 51, with the ROM lock 61 snapping to its original predetermined shape prior to being installed over the tab 46.

While the ROM lock 61 may be made from nylon, other materials may be used that can deflect and resiliently return to an original, predetermined shape or configuration once relaxed. Once the ROM lock 61 engages with the carriage 45, the ROM button 41 is prevented from being pulled away from the hinge by confining the pin 52 to the bottom (locked) location of the pin slot 54.

Figure 8D:
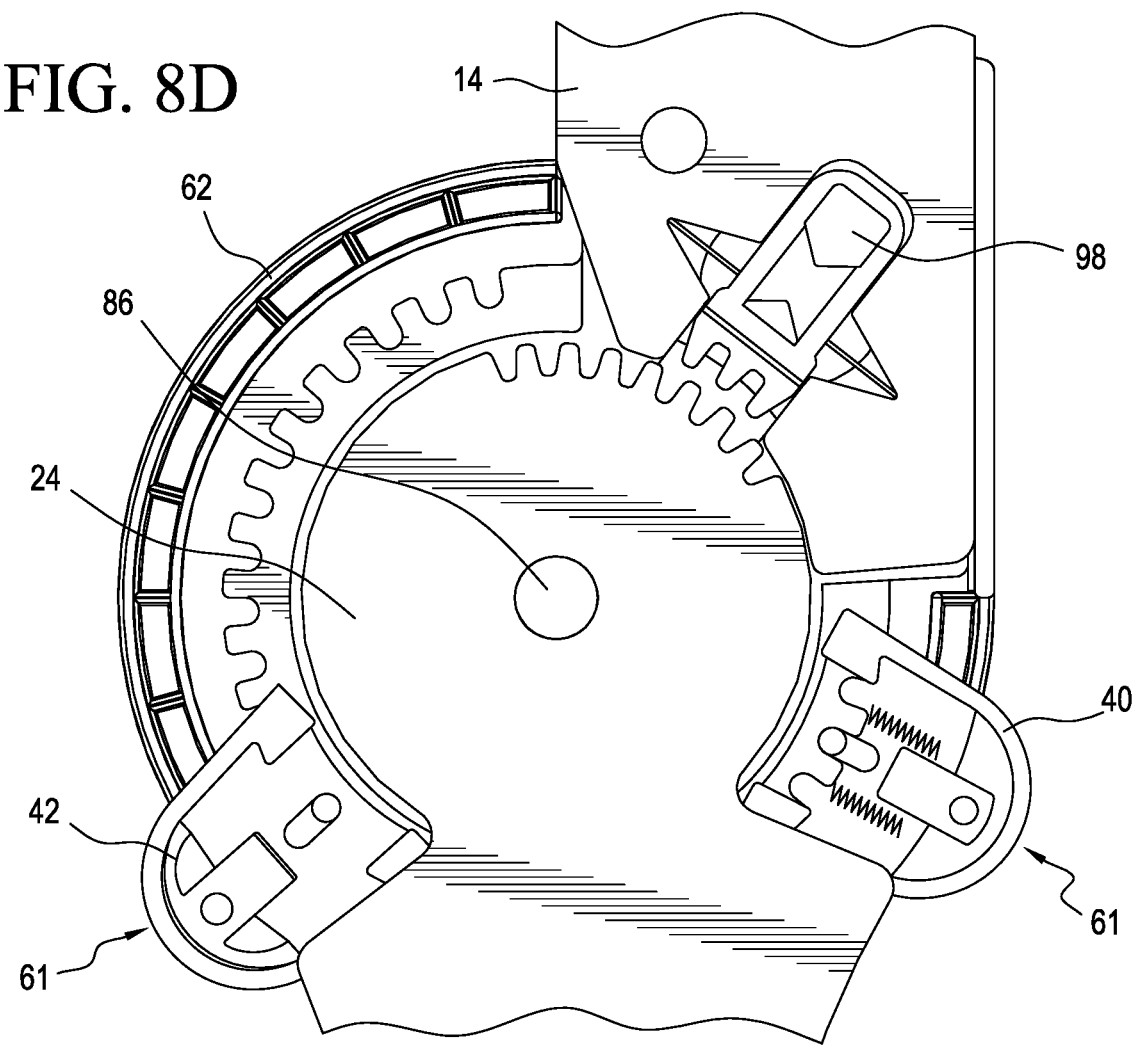
FIG. 8D illustrates an exemplary cross-section of the hinge of FIGS. 2 and 3 with the lock of FIG. 8A applied over the ROM buttons.

FIG. 8D shows a cross section of the hinge with the ROM lock 61 in place over the ROM buttons 40, 42, with the ROM locks 61 sufficiently within the first and second covers 60 (shown above), 62. The ROM lock 61 can be arranged to engage the first and second covers 60 (shown above), 62 along the circular rim or with a metal insert within the hinge.

Figure 9:
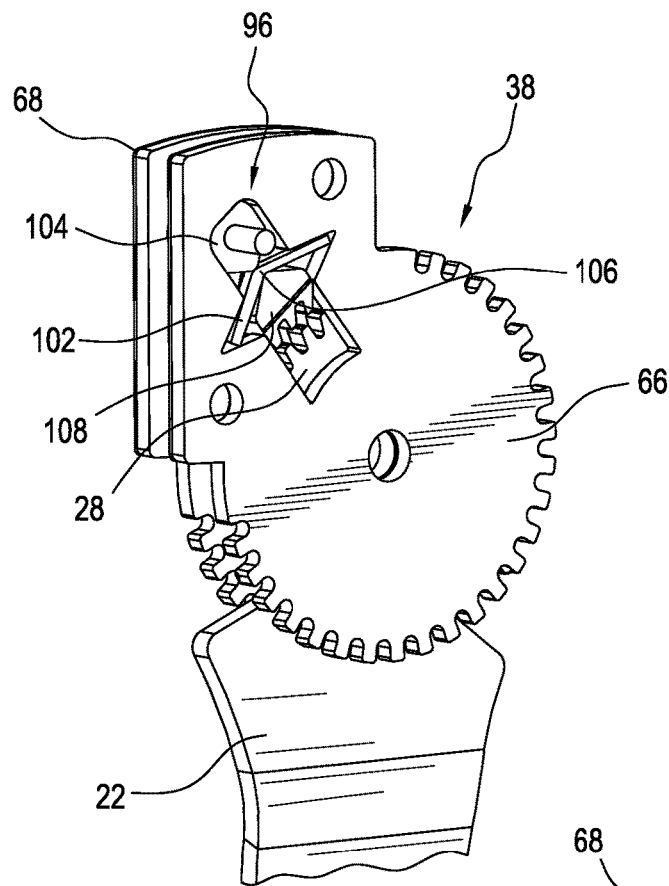
FIGS. 9 and 10 are perspective views of the pivot assembly showing the drop lock assembly in unlocked and locked positions, respectively.
Figure 10:
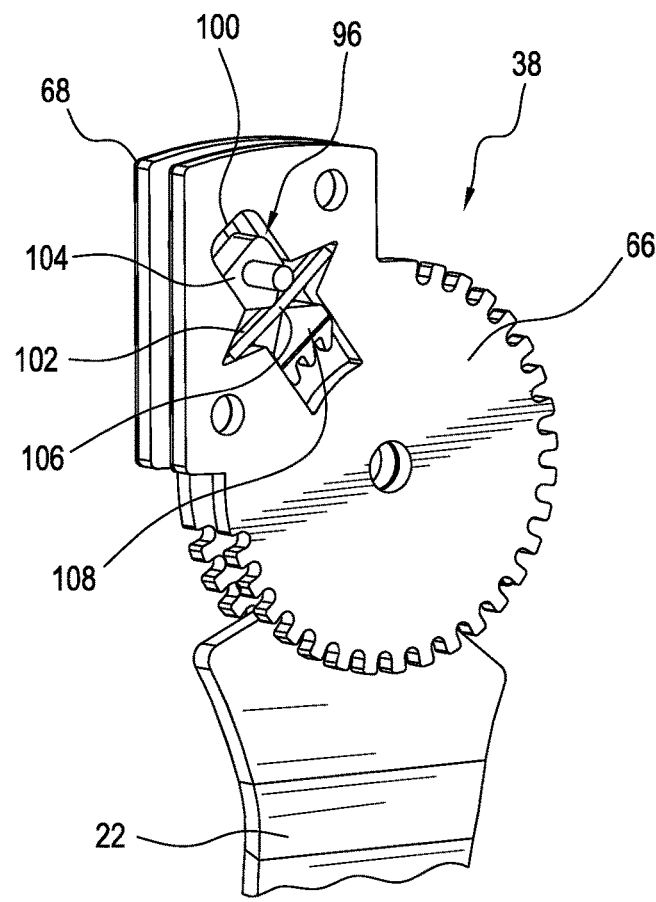

FIGS. 9 and 10 illustrate the pivot assembly 38, showing the drop lock assembly 96 with drop lock button 98 removed. The drop lock assembly 96 includes a drop lock body 104 shaped to define a groove 106 for engaging with a leaf spring 102. As shown, the drop lock body 104 and leaf spring 102 are slidably disposed within the drop lock recess 100. The groove 106 allows the leaf spring 102 to flex between two positions within the drop lock recess 100 corresponding to the locked and unlocked positions of the drop lock assembly 96.

FIG. 9 illustrates the drop lock assembly 96 in an unlocked configuration, with the leaf spring 102 deflected upward toward the upper strut (shown above) and away from the notches 28 of the lower strut 22. FIG. 10 illustrates the drop lock assembly 96 in a locked configuration, with the leaf spring 102 deflected downward toward the notches 28 (shown above). In the locked position, the leaf spring 102 maintains the drop lock body 104 downward so the lock teeth 108 engage with the notches 28.

Figure 11:
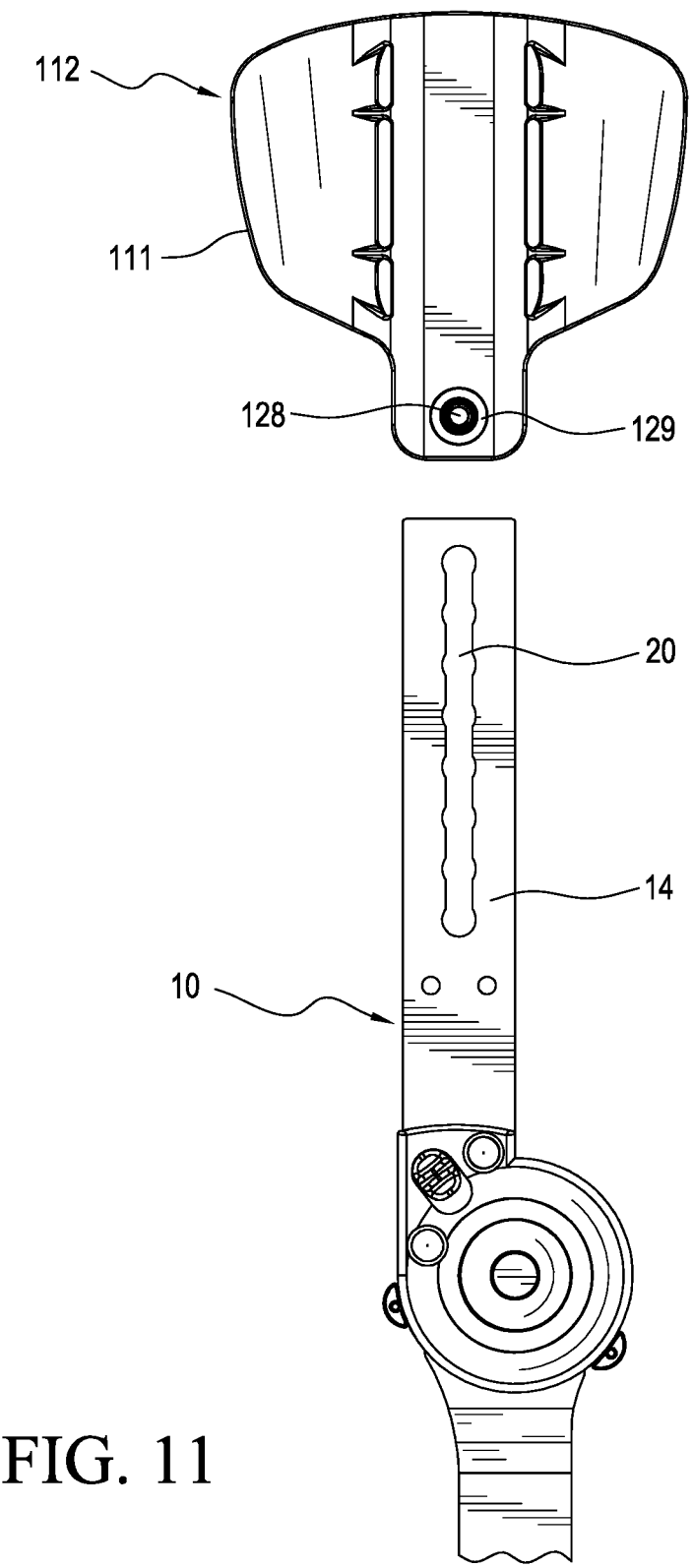
FIGS. 11-13 illustrate an exemplary paddle assembly and corresponding paddle lock mechanism of the first upright assembly.
Figure 12:
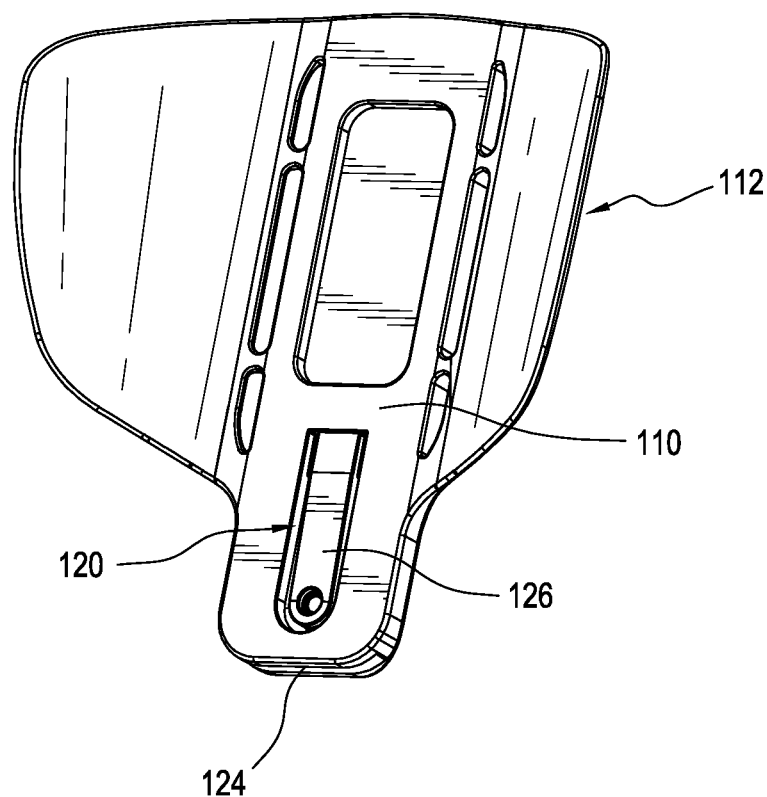
Figure 13:
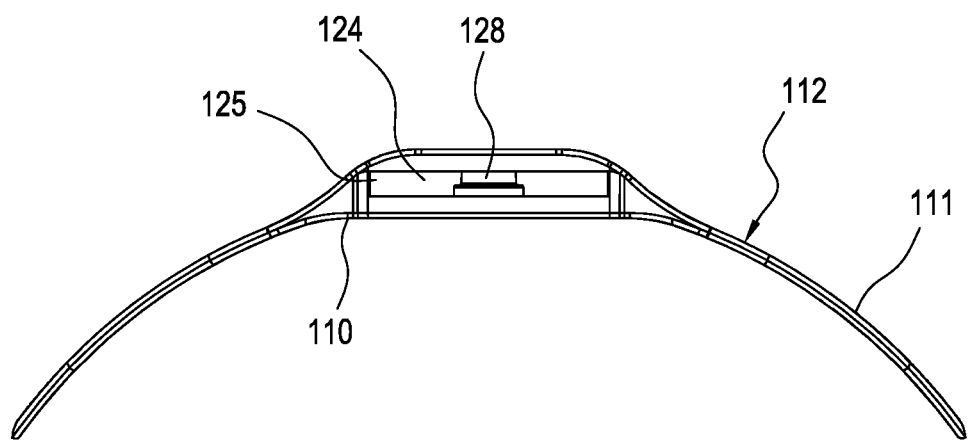

FIGS. 11-13 illustrate an exemplary first upper paddle assembly 112 and associated lock mechanism 120. Other paddle assemblies described herein may be similarly configured. The first upper paddle assembly 112 is configured for adjustable connection to a corresponding strut (in this exemplary instance, upper strut 14). An adjustment aperture 20 includes a number of wider sections configured to receive a post 128, spaced apart by several narrower sections too narrow for passage of the post 128. The upper strut 14 is inserted into the first upper paddle assembly 112 through a paddle slot 124 leading to an interior paddle channel 125. As depicted, the locking mechanism includes a lever 126 disposed on an inner paddle surface 110. The lever 126 is coupled to the post 128, which extends outward from the lever 126 through the interior paddle channel 125 to a post opening 129 disposed on the outer paddle surface 111. The lever 126 functions to bias the post 128 outward, such that the post traverses the interior paddle channel 125.

In operation, the first upper paddle assembly 112 may be adjusted when a user depresses the post (i.e., presses the post inward) through the access given by the post opening 129. Once the post has been depressed to a degree sufficient to clear the adjustment aperture 20, the first upper paddle assembly 112 may be freely translated upon the upper strut 14. If no further depression of the post 128 is provided, the first upper paddle assembly 112 may be translated until the post 128 aligns with a wider portion of the adjustment aperture 20, at which point the lever 126 will function to bias the post 128 outward into the wider portion of the adjustment aperture 20, preventing further translation and locking the first upper paddle assembly 112 into position.

Figure 14A:
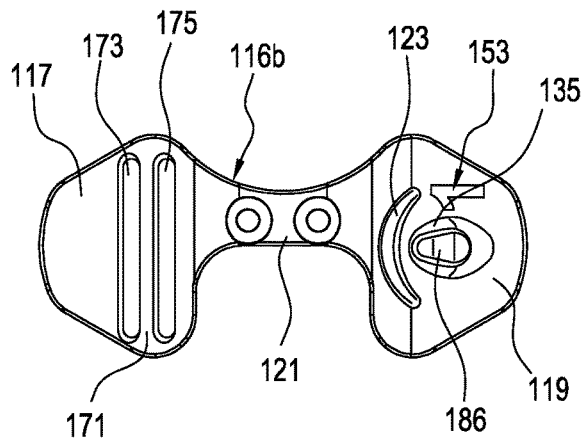
FIGS. 14A and 14B illustrate an embodiment of the first lower paddle assembly.
Figure 14B:
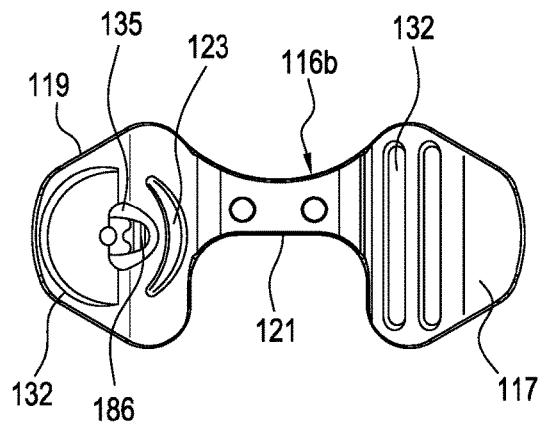

FIGS. 14A and 14B exemplify another embodiment of the second lower paddle assembly 116b. Similar to the second lower paddle assembly 116a in the embodiment of FIG. 1, the second lower paddle assembly 116b includes first and second wings 117, 119, spaced apart by a central portion 121. The first wing 117 includes a first attachment member 171 dividing first and second strap slots 173, 175, and is adapted to support a strap 190, as shown in FIG. 16. The central portion 121 is arranged to secure to the lower strut 22 in FIG. 1. The second wing 119 defines a coupling member 186 arranged over an opening 135 and proximate to a relief opening 123.

A rear surface of the second wing 119, as shown in FIG. 14B, about the coupling member 186 may be reinforced to provide better support to the second lower paddle assembly 116b while a strap is secured thereto. The reinforcement may be defined as a thickened region 137 on an opposed side from the relief opening 123. The front surface or other suitable areas of the second wing 119 may be reinforced, and the above reinforcement area 151 is by example.

In the illustrated example, the relief opening 123 has an arcuate shape but is not limited to such shape, however the arcuate shape is advantageous because the second lower paddle assembly 116b is bent at its corners and preserves a "snapping" geometry of the coupling member 186. The relief opening 123 allows the second lower paddle assembly 116b to maintain flexibility, particularly as a strap is secured and tensioned between the first and second wings 117, 119, but inhibits deformation of the second lower paddle assembly 116b as a whole. The relief opening 123 enables the remainder of the second lower paddle assembly 116b to be thickened and strengthened while providing sufficient flexibility to the user by yielding proximate the coupling member 186.

Figure 15A:
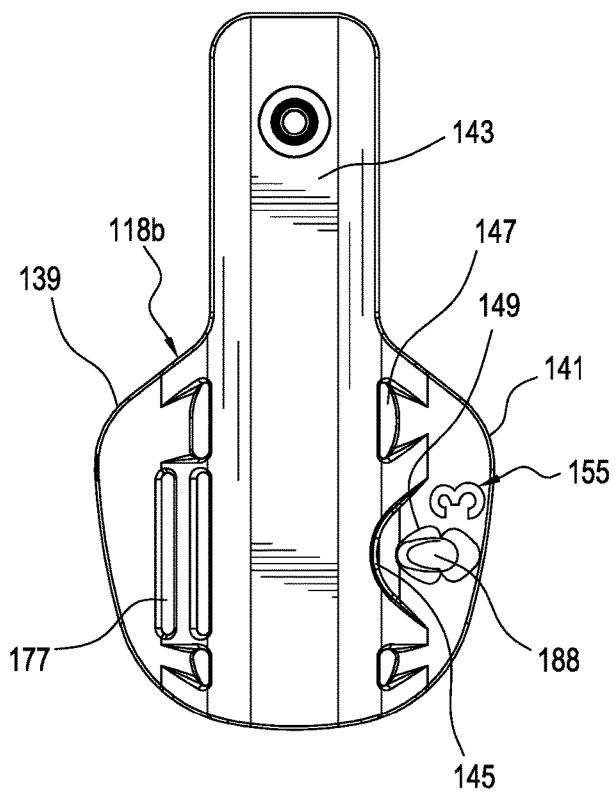
FIGS. 15A and 15B illustrate an embodiment of the second lower paddle assembly.
Figure 15B:
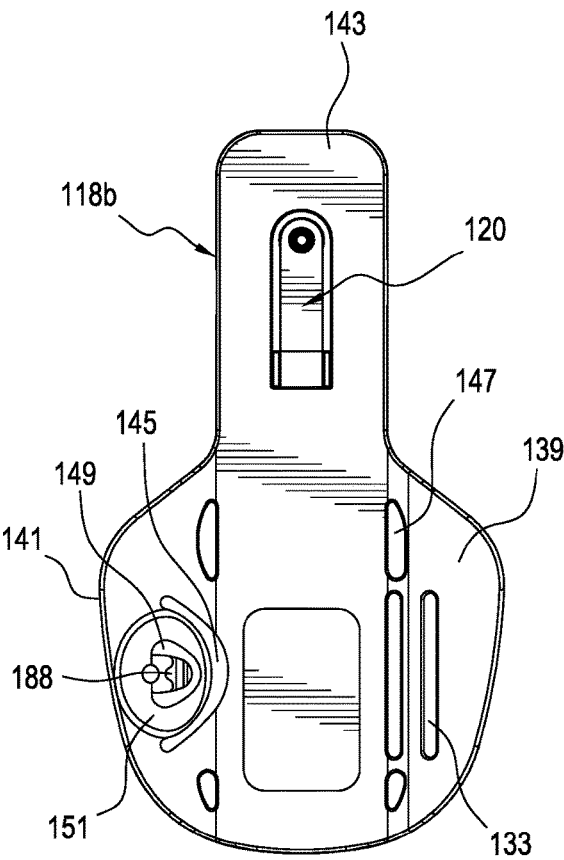

FIGS. 15A and 15B exemplify another embodiment of a first lower paddle assembly 118b. As with the second lower paddle assembly 116b, the first lower paddle assembly 118b includes first and second wings 139, 141, spaced apart by a central portion 143. The first wing 139 includes a first attachment member 177 dividing strap slots, and is adapted to support a strap 192 in FIG. 16. The central portion 143 is adapted to secure to the lower strut 22 in FIG. 1.

The second wing 141 defines a coupling member 188 arranged over an opening 149 and proximate to a relief opening 145. Both the first and second wings 139, 141 define apertures along the central portion 143, for enabling flexure of the wings 139, 141 relative to the central portion 143 and arranged above and below the first attachment member 177, and the coupling member 188 and relief opening 145, without hindering the first attachment member 177 and the coupling member 188. The second wing 141 includes an exemplary reinforcement area 151 similar to the second lower paddle assembly 116b.

Each of the first and second lower paddle assemblies 118b, 116b, include indicia for advising a user of a preferred sequence for securing straps, as shown in FIG. 16. The indicia may be printed, such as with a number, color or pattern of features, or formed on the first and second lower paddle assemblies 118b, 116b. A strap associated with the second lower paddle assembly 116b is the first strap to be applied to a user, by indication of indicia "1" on the second lower paddle assembly 116b. Another strap is associated with the first lower paddle assembly 118b, and is the third strap to be applied to a user, by indication of indicia "3" on the first lower paddle assembly 118b.

Figure 16A:
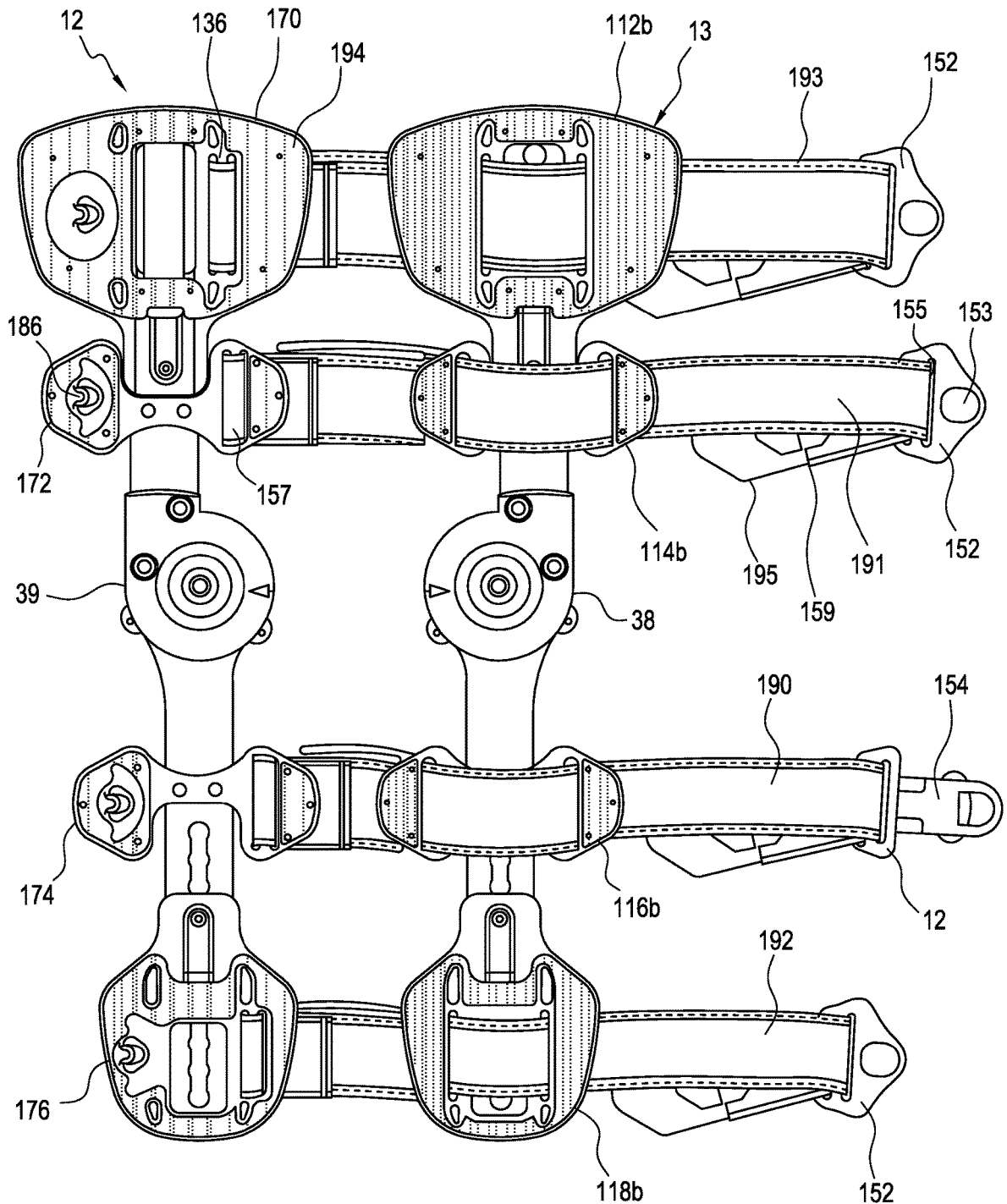
FIG. 16A illustrates a perspective view of a variation of the orthopedic device of FIG. 1 with strap assemblies.

FIG. 16A shows an exemplary arrangement of the orthopedic device of having first and second upper paddle assemblies 112b, 114b, similar to the first and second lower paddle assemblies 118b, 116b of FIGS. 14a-15b. Straps 190, 191, 192, 193 are associated with various paddle assemblies according to the indicia or preferred sequence of donning the orthopedic device on a user. Hook fastener material 194 or other suitable fastener material is applied to each of the paddle assemblies for securing to pads.

Figure 16B:
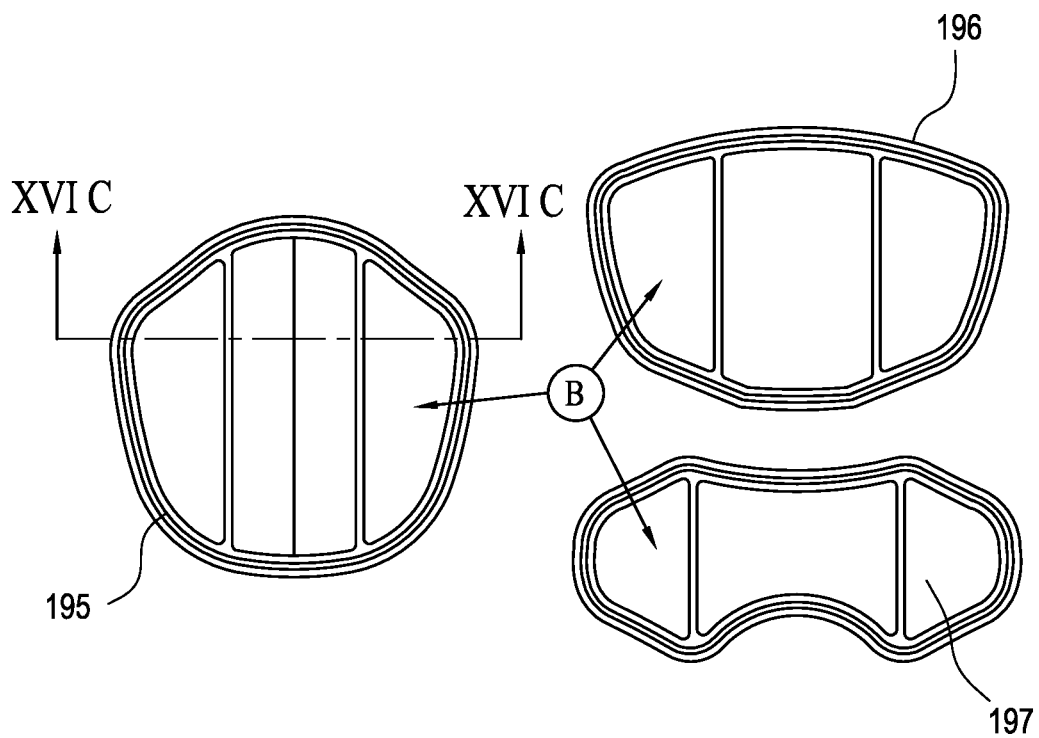
FIG. 16B illustrates various pads for use with the strap assemblies in FIG. 16A.

FIG. 16B shows exemplary pads 195, 196, 197 arranged for securing to respective paddle assemblies. Each of the exemplary pads 195, 196, 197 are cut or formed to correspond in shape to its respective paddle assembly. The pads 195, 196, 197 are preferably formed from a foam or other suitable compressible material, and have a surface lined with unbroken loop material or other suitable material for securing to the hook fastener material 194.

Figure 16C:
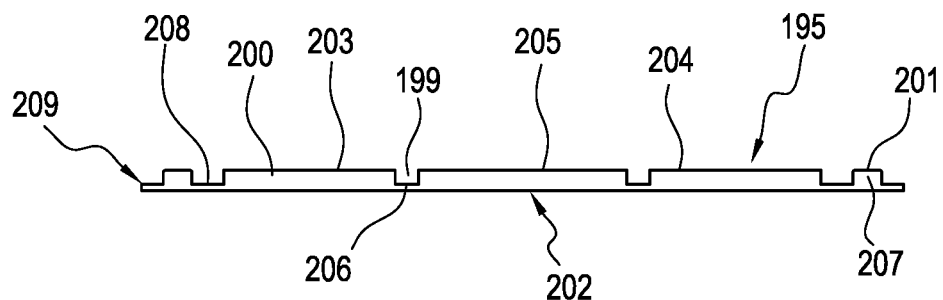
FIG. 16C is a cross-section of the pad in FIG. 16B taken along line XVIC-XVIC.

FIG. 16C shows a cross-section of exemplary pad 195 having a plurality of hinges 199 formed by weld lines that correspond to opposed sides of the central portion in the first lower paddle assembly 118b, as shown in FIGS. 15a and 15b. Any of the aforementioned pads may be formed similarly to the pad 195, and according to the structure of the paddle assembly by which they lie against. The hinges 199 follow the first and second wings 139, 141, such that the pad 195 has first and second pad wings 203, 204 separated from a central pad portion 205 by the hinges 199. Each of the pad wings and the central pad portion 205 have a greater thickness area 200 than the hinges 199 defined by thinner thickness areas 206, preferably formed by thermoforming foam.

The pad 195 defines thermoformed edge area 201 defined by a thicker region 207 of the pad, and bordered by a hinge 208 adjacent the pad wings 203, 204, and a peripheral edge area 209 having a thickness thinner than the thicker region 201. The edge area 201 preferably surrounds the first and second pad wings 203, 204, and the central pad portion 205. The edge area 201 provides pressure relieving areas about the periphery of the pad 195, and the peripheral edge area 209 and hinge 208, assist in enabling the pressure relieving area, and add to overall comfort of the pad 195.

Figure 16D:
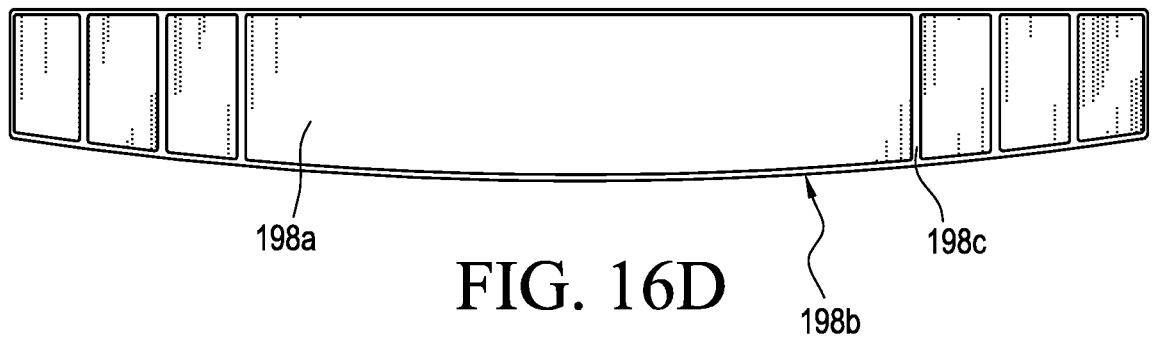
FIG. 16D is an exemplary view of an anti-migration strap.

FIG. 16D illustrates an exemplary strap 198a that may replace strap 190 or may overlie the strap 190 associated with the second lower paddle assembly 116b. The strap 198a may serve as an anti-migration strap and preferably includes weld lines 198c useable for trimming the length of the strap 198a. A center portion 198b may be thermoformed to shape.

Figure 17:
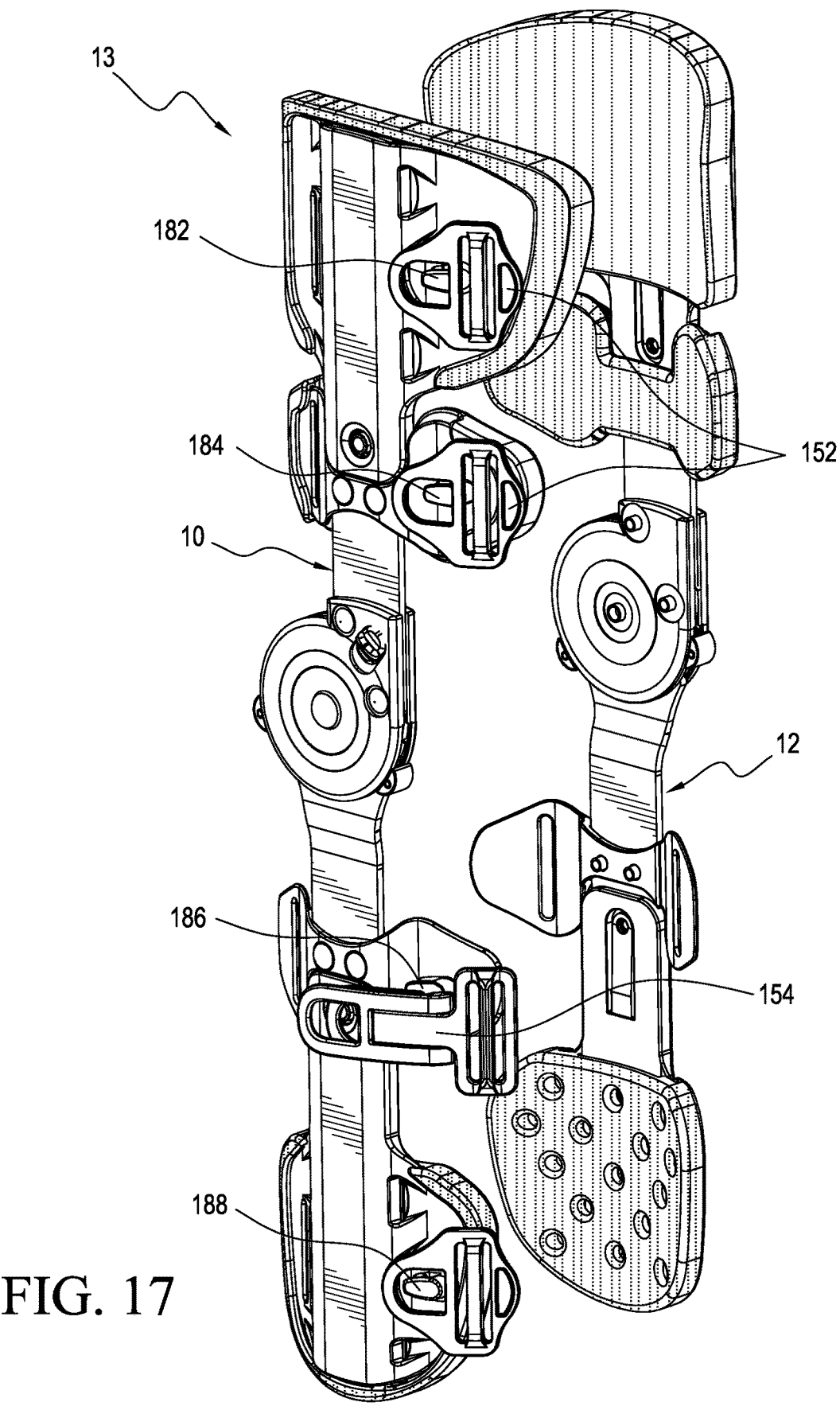
FIG. 17 illustrates clasps and clasp coupling members of the knee brace of FIG. 1, including a lever fastener.

FIG. 17 illustrates an exemplary knee brace 13, showing clasp coupling members 182, 184, 186, 188. The knee brace 13 may also include one or more clasps configured to couple with the clasp coupling members, such as the illustrated D-ring clasps 152. Straps may be secured and guided by various components of the knee brace 13 to enable fitting of the brace to a user, and the straps may be attached to clasps, such as those illustrated, to provide circumferential closure of the brace around the user's leg when the clasps are coupled to corresponding clasp coupling members. One or more clasps may be configured as lever fasteners.

In the illustrated embodiment, a lever fastener 154 or clasp assembly is positioned to clasp a strap enclosing the upper portions of the calf. Often this is an area where migration and slippage of a donned brace occur, and is often an area that can be difficult to appropriately tighten in a consistent manner. Although this exemplary embodiment depicts only one such lever fastener 154, one or more of the other clasps may also be configured as lever fasteners.

Figure 18:
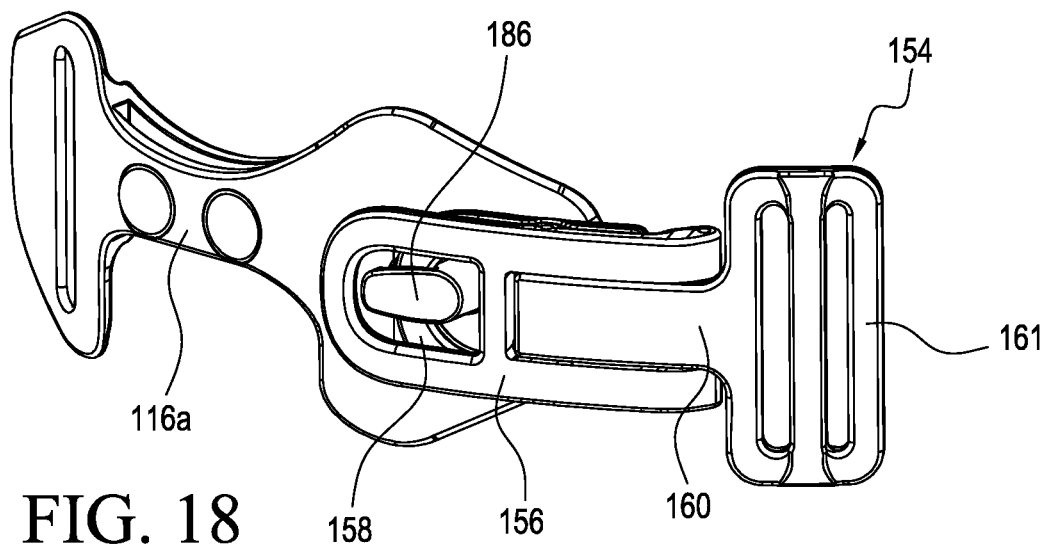
FIGS. 18-20 illustrate operation of the lever fastener of FIG. 16.
Figure 19:
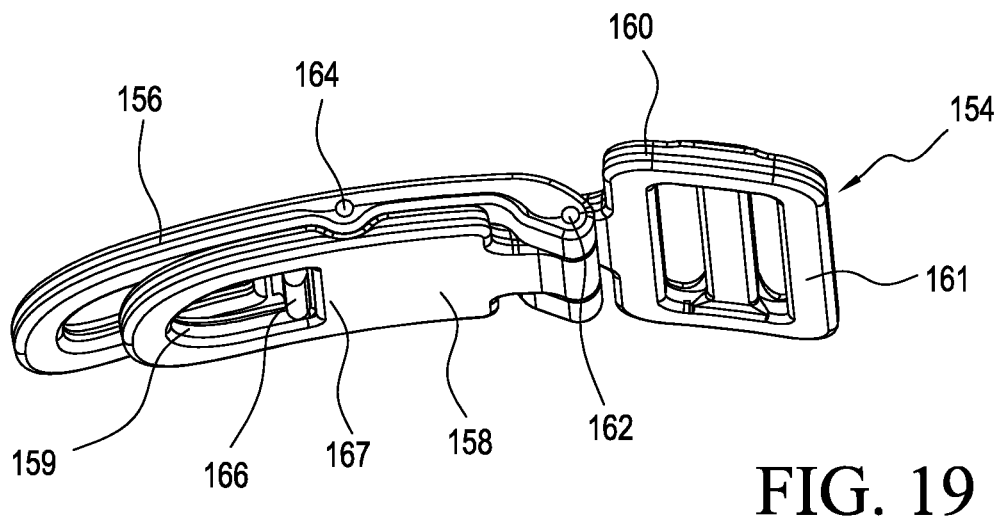
Figure 20:
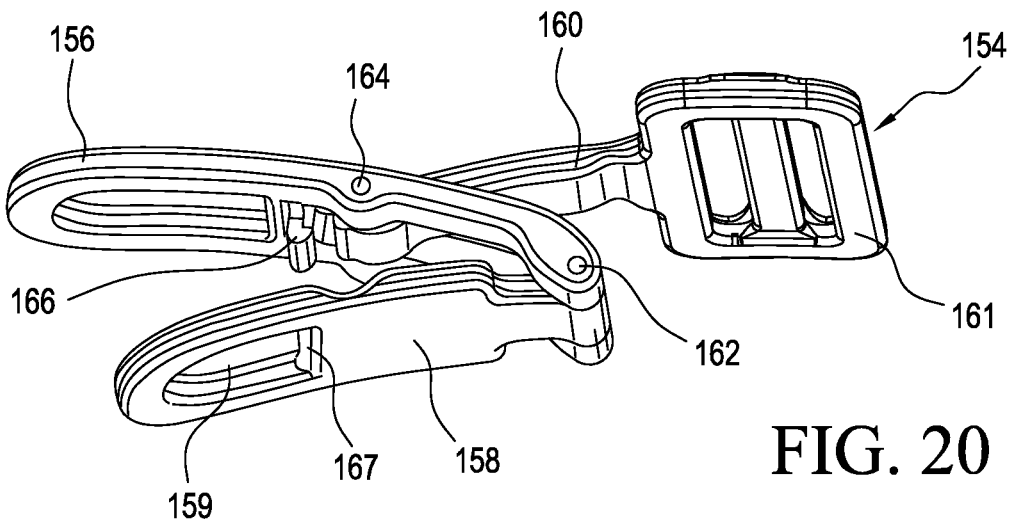

FIGS. 18-20 illustrate operation of lever fastener 154. FIG. 18 illustrates the lever fastener 154 coupled to a second lower paddle assembly 116a. The lever fastener 154 includes a fastener portion 158 configured to couple with a corresponding clasp coupling member 186. In the illustrated embodiment, the fastener portion 158 is formed as a D-ring. The fastener portion 158 is joined to a handle portion 156 at a first hinge 162. The handle portion 156 is rotatable regarding the fastener portion 158 about the first hinge 162. The illustrated handle portion 156 has a length that extends from the first hinge 162 beyond the length of the fastener portion 158 when the lever fastener 154 is in the closed configuration shown in FIG. 19. The handle portion 156 is configured to allow a user to actuate the lever fastener 154 between the opened and closed configurations without interfering with coupling of the fastener portion 158 to a corresponding coupling member 186.

The handle portion 156 includes a clip 166 that extends toward the fastener portion 158 and that is configured to engage with the fastener portion 158 to lock the handle portion 156 in the closed configuration. The clip 166 is configured so that when a sufficient moment force is applied about the first hinge 162, the clip 166 disengages from the corresponding surface of the fastener portion 158 to allow the handle portion 156 to rotate about the first hinge 162. In this embodiment, a non-curved portion of a D-ring 159 of the fastener portion 158 functions as a clip attachment surface 167.

The handle portion 156 is joined to a strap attachment portion 160 about a second hinge 164. The second hinge 164 allows the strap attachment portion 160 to be rotated relative to the handle portion 156. As shown, the strap attachment portion 160 is shaped to fit within a matching profile area of the handle portion 156, such that when the lever fastener 154 is in the closed configuration, the strap attachment portion 160 nests partially within the handle portion 156 to maintain a low profile and a smooth outer surface of the lever fastener 154. The low profile design beneficially reduces bulk and lowers the risk of inadvertently catching the lever fastener 154 upon an object.

When the lever fastener 154 is moved toward the open configuration in FIG. 20, the distance between the fastener portion 158 and the strap attachment portion 160 is increased. The distance between the D-ring 159 of the fastener portion 158 and the strap attachment member 161 of the strap attachment portion 160 may be increased.

In operation, a strap (not shown) is attached to the strap attachment member 161. When a user (or physician/fitting therapist or other user) desires to attach the strap to the second lower paddle assembly 116a to complete the encircling of the strap about the leg, the user may couple the D-ring 159 to the corresponding clasp coupling member 186. Beneficially, by placing the lever fastener 154 in the open configuration during this coupling, the strap may be provided with an increased amount of slack, making it easier to couple the fastener portion 158 to the clasp coupling member 186 with no pulling and over-tightening to bring the D-ring 159 past and then into the receiving area of the clasp coupling member 186.

The lever fastener 154 may then be moved to the closed configuration shortening the distance between the clasp coupling member 186 and the strap attachment member 161 and tightening the strap accordingly. This allows the strap to be easily fitted to the appropriate tightness without the need to adjust placement or attachment of the strap itself relative to the lever fastener 154. This also allows the strap to be consistently applied at the same tightness while also providing easy detachment and reattachment. This is beneficial where a brace is frequently donned and doffed, and reduces the amount of readjusting necessary to maintain a consistent fit.

Figure 21:
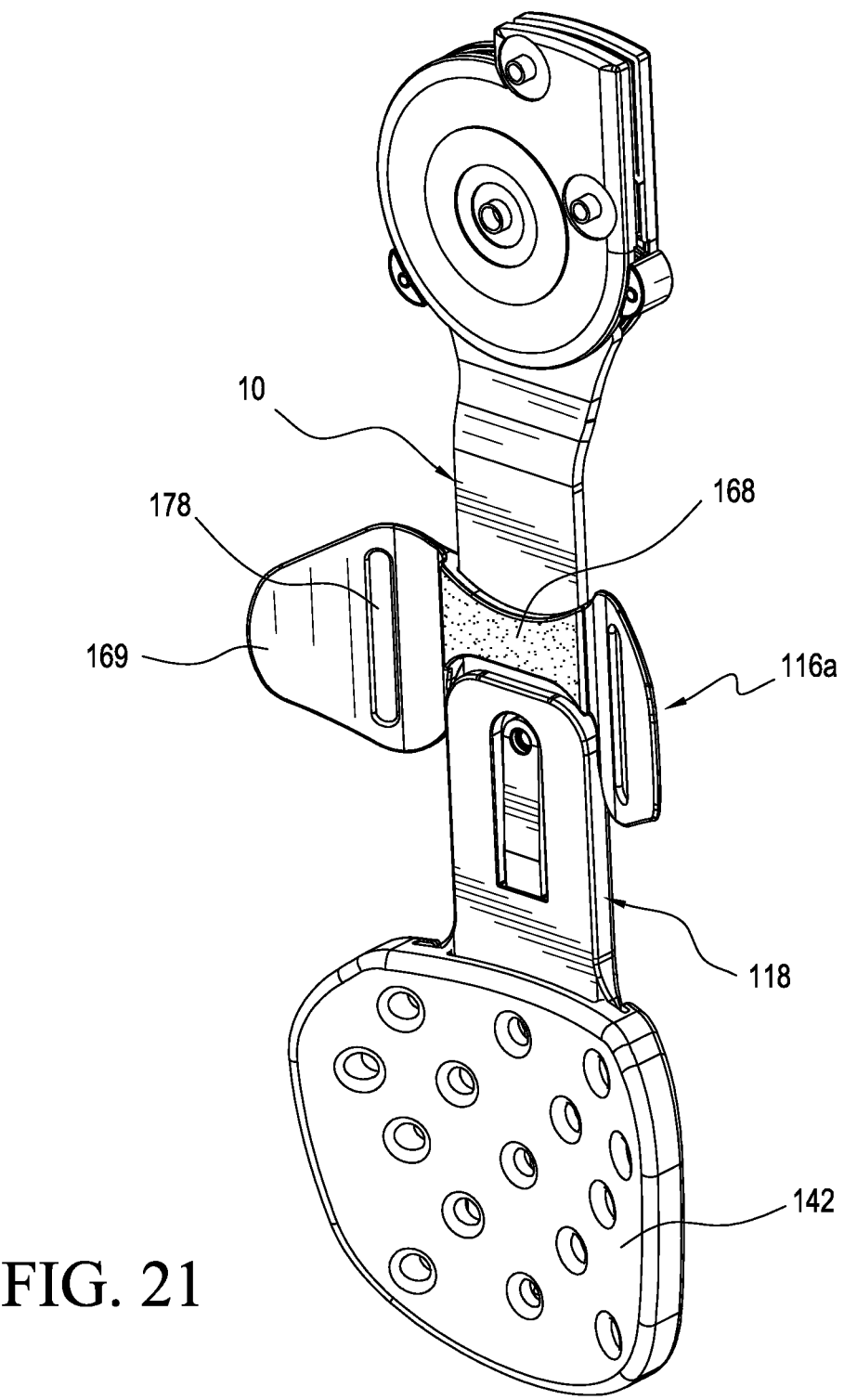
FIG. 21 illustrates an inner side of the first upright assembly of FIG. 1.

FIG. 21 shows a view of the inner side of the upright assembly 10. As shown, the pad 142 includes a number of holes configured to add to the breathability of the pad 142. A knee brace may include one or more of such pads and/or may include one or more pads configured with ridges, perforations, striations, or other features for increasing the texture/gripability and/or breathability of the pads.

FIG. 21 shows the first lower paddle assembly 118b as including an integrated fastener portion 168 disposed on the inner side 169 of the first lower paddle assembly 118b. One or more of the paddle assemblies of a brace may include such integrated fastener portions, which may be formed as integrated (e.g., injection molded or otherwise integrally formed) portions of hook fastener material. The integrated fastener portion 168 beneficially functions to lock a strap (e.g., one formed with corresponding loop fastener material)

against the inner side 169. A strap (not shown) may be passed through the strap guiding slots 178. Upon proper positioning of the strap, the strap may be attached to the integrated fastener portion 168, thereby locking the position of the strap relative to the upright assembly 10. In some embodiments, a blocking sheet (not shown) may be placed over the integrated fastener portion 168 to prevent attachment of the strap until it is desired, at which point the blocking sheet may be removed to allow contact between the hook and loop fastener materials.

Figure 22:
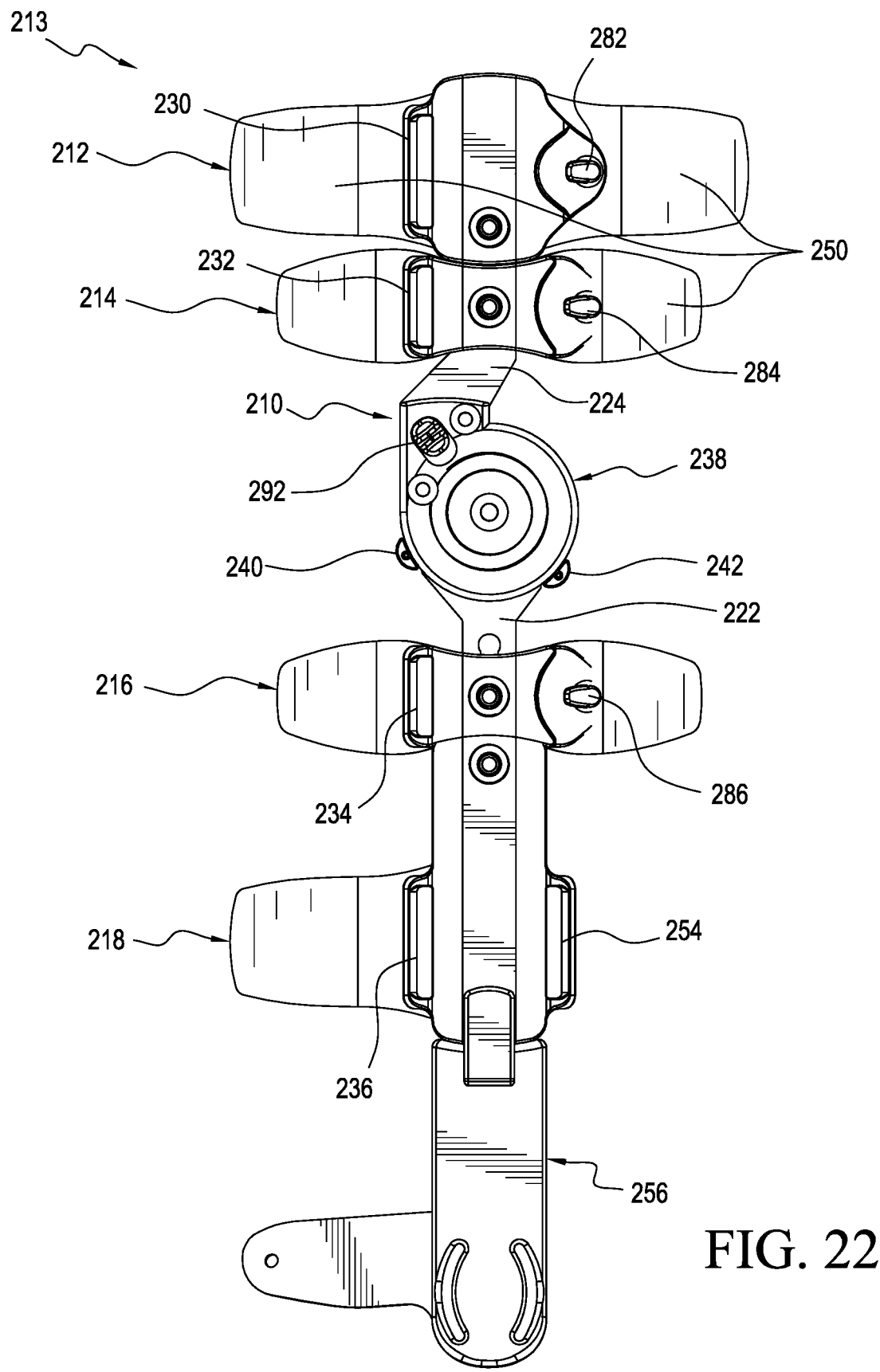
FIG. 22 is an elevational view of an upright assembly of an orthopedic device in an immobilization or post-operative elbow brace.

FIG. 22 illustrates an exemplary embodiment of an immobilization or post-operative elbow brace 213. The features and components of the post-operative elbow brace 213 may be configured similarly to the embodiments of the aforementioned knee brace features and components described herein. The illustrated post-operative elbow brace 213 includes an upright assembly 210 including an upper strut 224 and a lower strut 222 joined by a pivot assembly 238. The pivot assembly 238 includes pivot stops 240, 242 and a drop lock assembly 292 which operate similar to like components described in relation to the aforementioned knee brace embodiments. The illustrated post-operative elbow brace 213 includes paddles 212, 214, 216, 218 having formable sections 250 configured to be formable (e.g., formed from aluminum or similarly formable material) about the arm of a user to aid in fitting of the post-operative elbow brace 213.

The post-operative elbow brace 213 includes strap attachment members 230, 232, 234, 236 to which straps may be joined. Typically, in an elbow brace application, a user will don a single upright, with the straps extending from the strap attachment members 230, 232, 234, 236 around the arm and back to corresponding clasp coupling members, such as clasp coupling members 282, 284, 286. The illustrated embodiment also includes a sling strap coupling member 254 configured for attachment of a sling strap positionable over a user's opposite shoulder.

Figure 23:
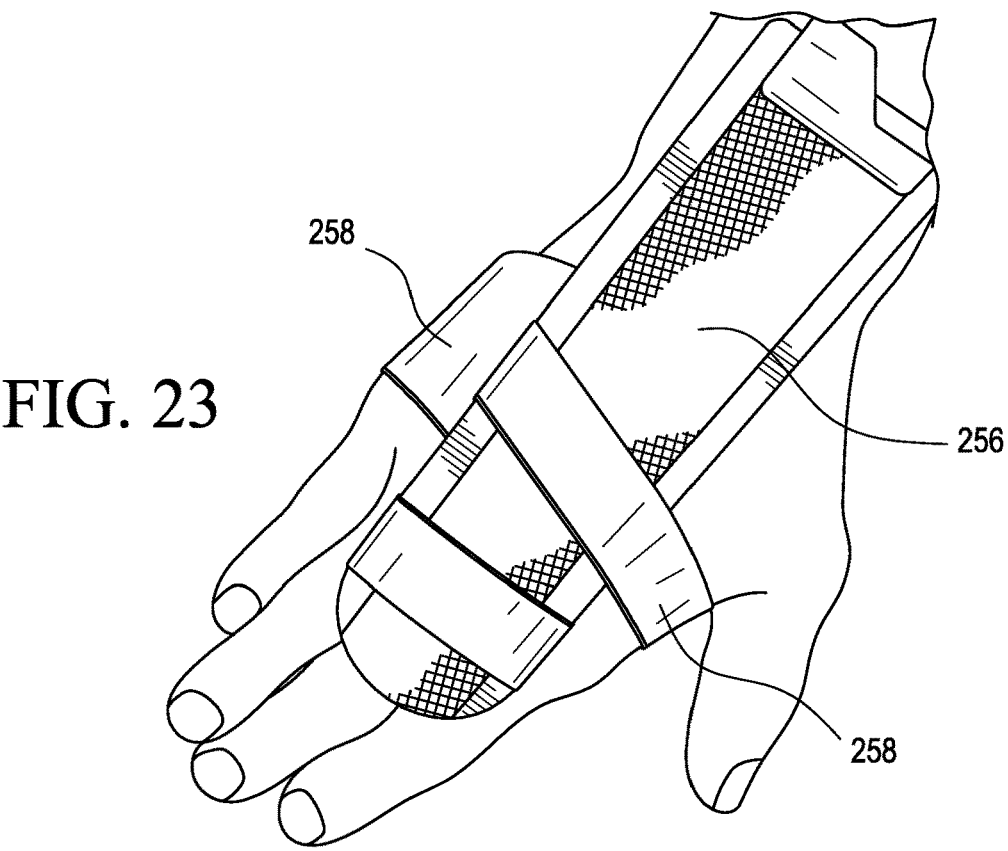
FIGS. 23-25 illustrate top, side, and profile views, respectively, of an optional wrist control usable with the elbow brace of FIG. 22.
Figure 24:
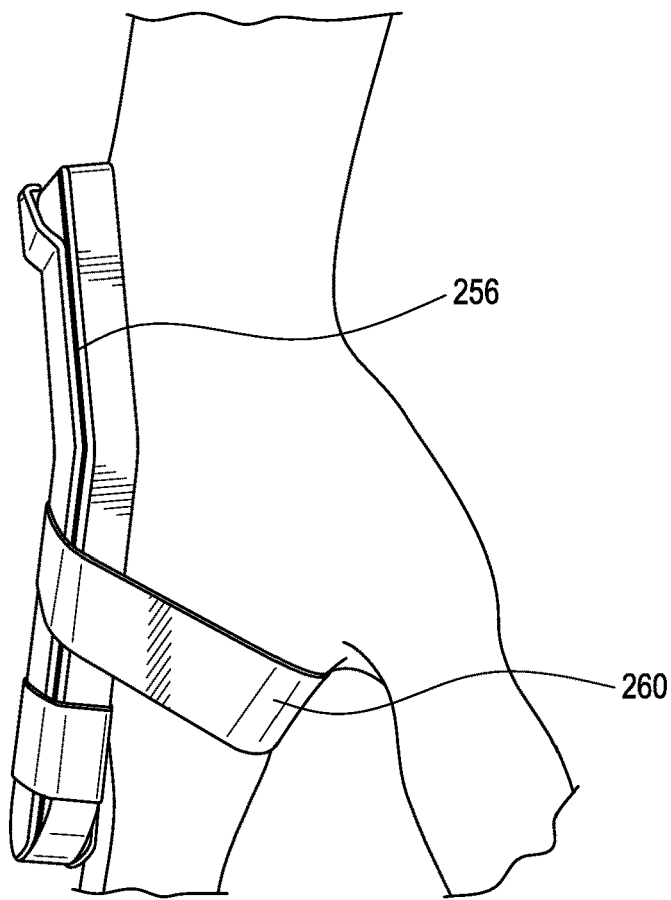
Figure 25:
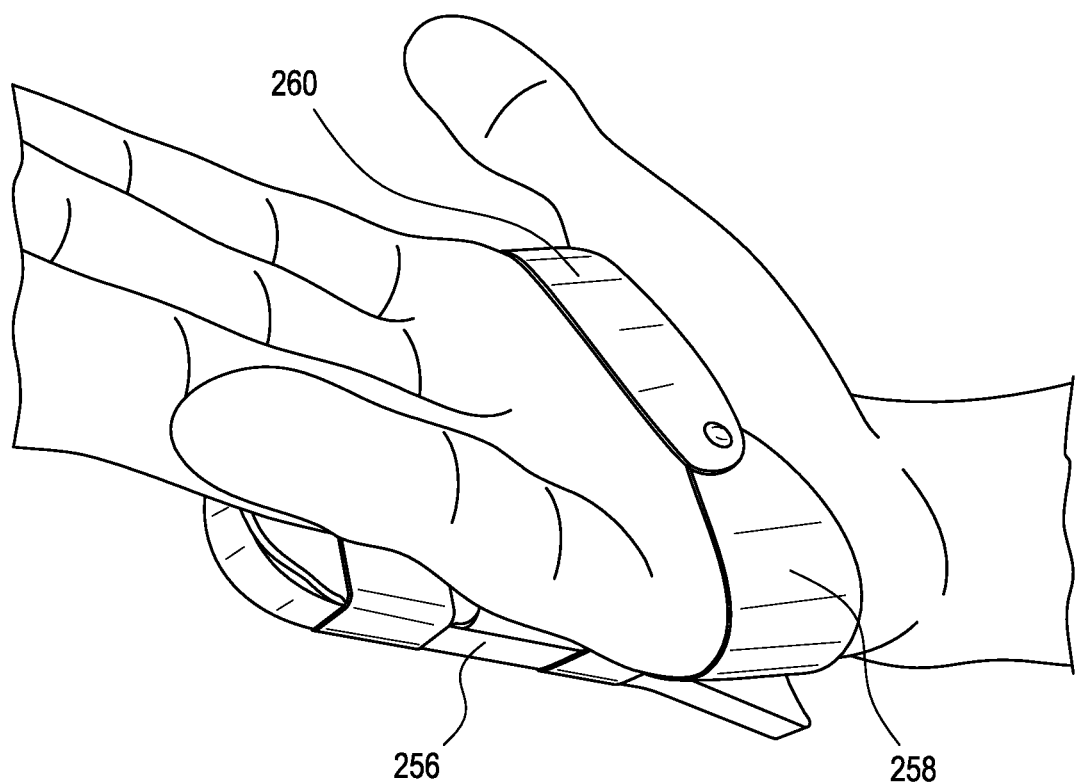

FIGS. 23-25 illustrate top, side, and profile views, respectively, of a wrist control 256 as worn by a user. The post-operative elbow brace 213 may include the optional wrist control 256 configured to immobilize or limit wrist movement of a user. As depicted, the wrist control 256 includes a first strap member 258 that reaches around the ulnar side of the user's hand and a second strap member 260 that reaches around the radial side of the user's hand (through the crook of the hand) to couple with the first strap member 258 at the palm of the user's hand.

Figure 26:
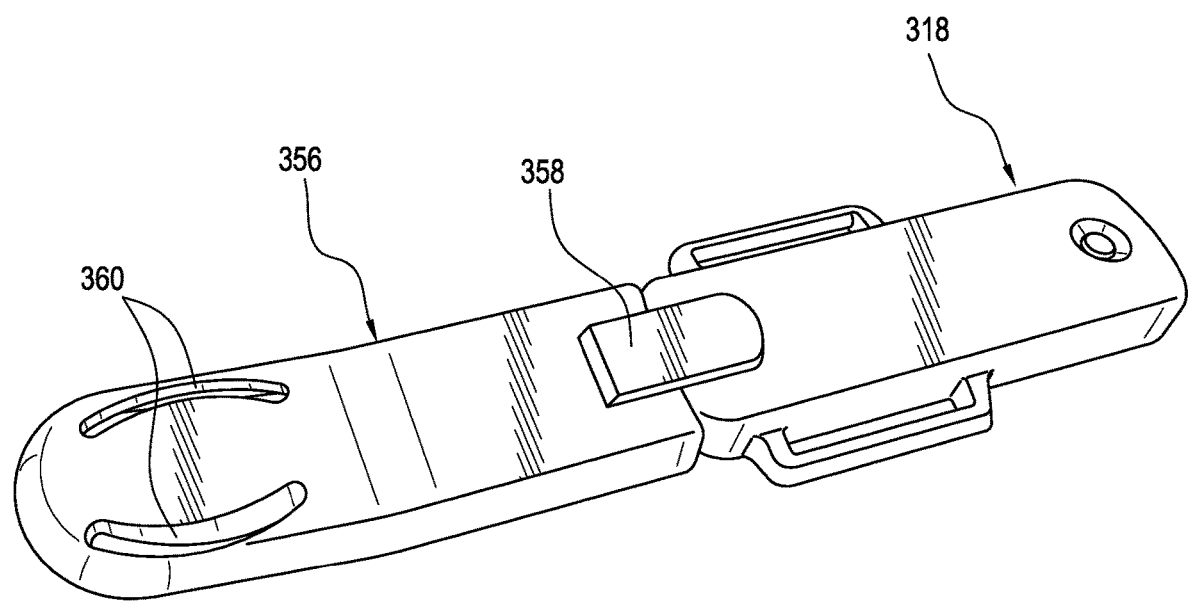
FIGS. 26-28 schematically illustrate a wrist control configured to immobilize or limit wrist movement of a user.
Figure 27:
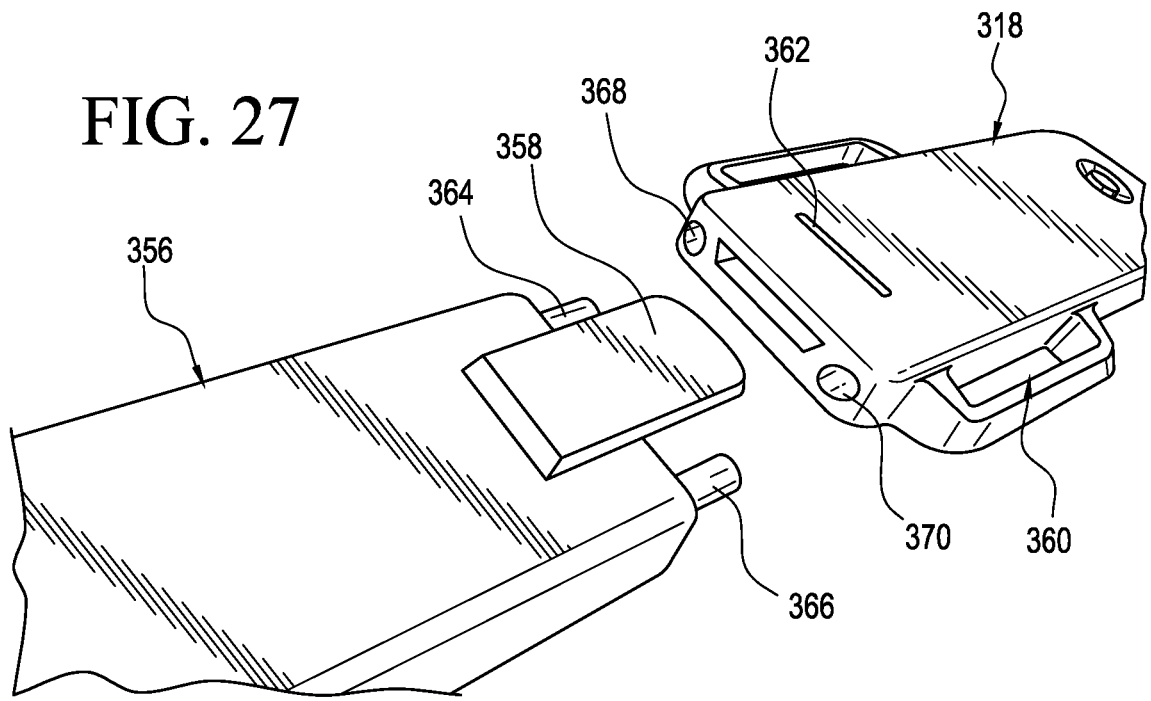
Figure 28:
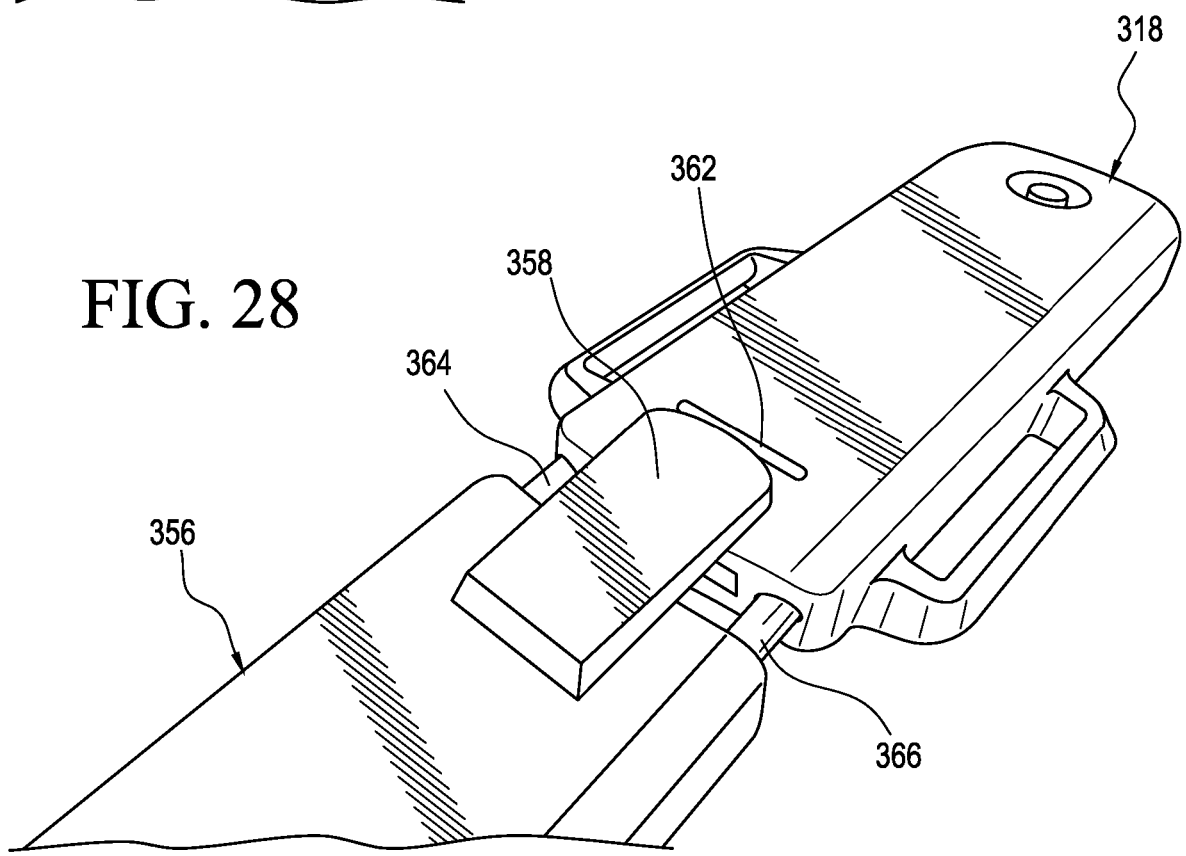

FIGS. 26-28 illustrate a wrist control 356 configured to immobilize or limit wrist movement of a user. As depicted, the wrist control 356 includes a clip 358 to enable attachment of the wrist control 356 to a corresponding clip receiver 362 of a paddle assembly 318. The illustrated wrist control 356 also includes strap slots 360 for receiving and guiding straps to fit the wrist control 356 to a user's hand. As depicted in FIGS. 27 and 28, the wrist control 356 also includes guides 364, 366 to enable aligned coupling to the paddle assembly 318 via corresponding guide holes 368, 370.

Figure 29:
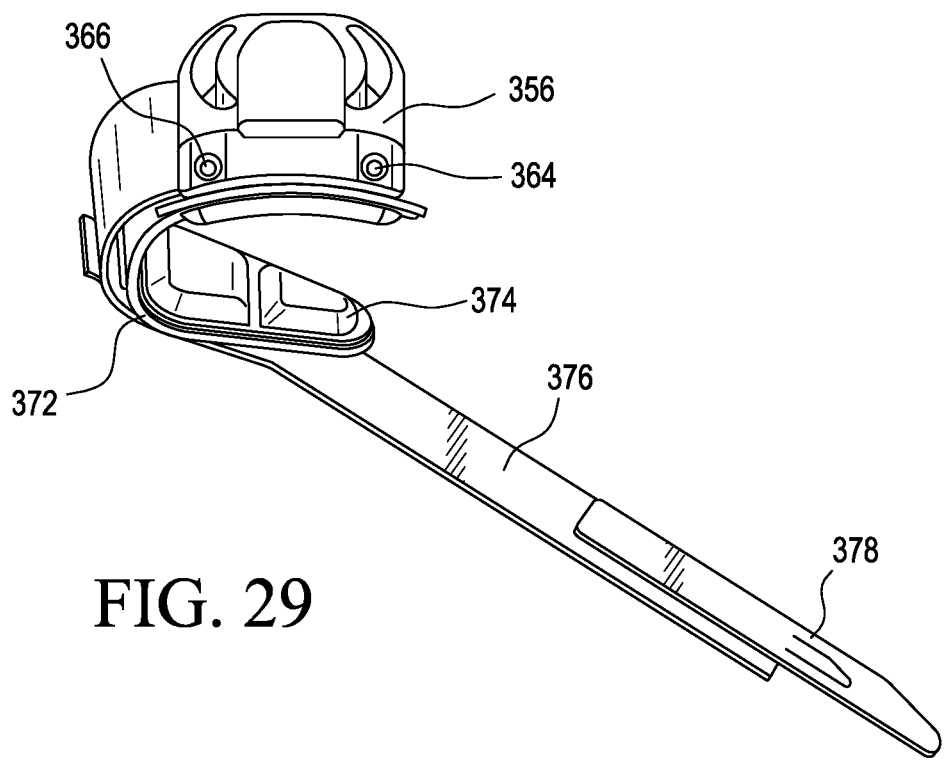
FIG. 29 illustrates a front elevational view of another embodiment of a wrist control.
Figure 30:
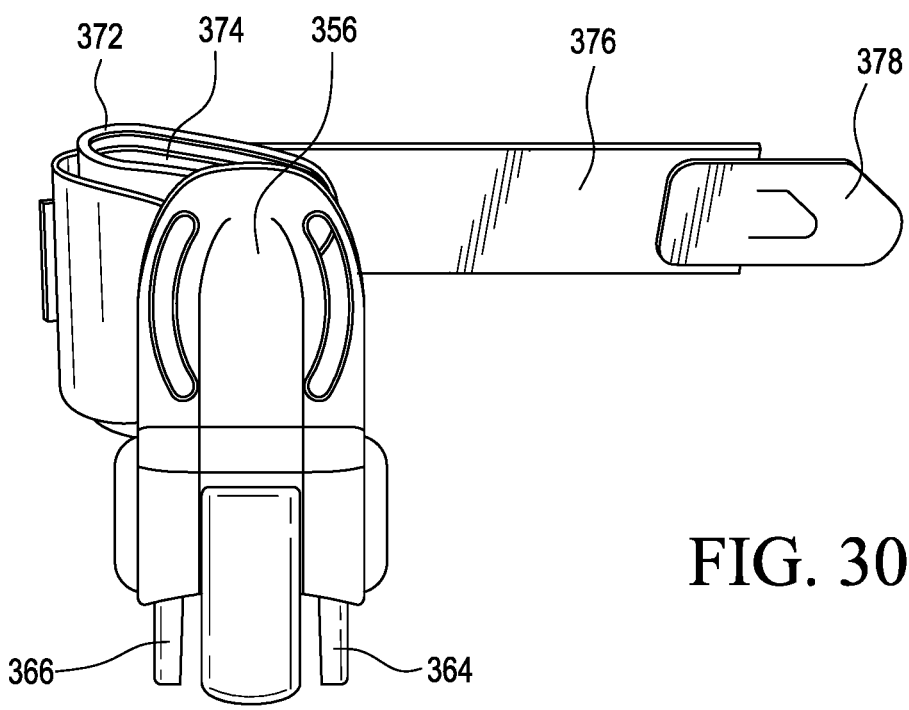
FIG. 30 illustrates a top plan view of the embodiment of FIG. 29.

FIGS. 29 and 30 exemplify a variation of the wrist control 356 with a stay 372 attached thereto. The stay 372 may be formed from cold-formable aluminum enabling a clinician to adjust the shape of the stay 372 to fit anatomy of a user while preserving its shape, or alternatively it may have a predetermined, fixed shape. Padding 374 may line the stay 372, and a strap 376 may connect to either the wrist control 356 or the stay 372, and have a tab 378 for securing to the strap 376 or the wrist control 356.

An advantage to the wrist control 356 is that the stay 372 can be removed, reversed and reattached to the wrist control 356 so the post-operative elbow brace 213 can be arranged for right- or left-handed use.

While the foregoing embodiments have been described and shown, alternatives and modifications of these embodiments, such as those suggested by others may be made to fall within the scope of the disclosure. While the orthopedic device has mostly been described in relation to an immobilization or post-operative knee brace, it will be understood that the principles, features, and/or components described may be extended to other types of orthopedic and prosthetic devices.

The invention claimed is:

1. An upright assembly for an orthopedic device, the upright assembly comprising at least a first strut connected to a second strut by a hinge, wherein the upright assembly further comprises:

a first paddle assembly having a lock mechanism, the first paddle assembly adapted to slide along the first strut and adjustably lock to the first strut among a plurality of predetermined locations by the lock mechanism, the first strut forming an adjustment aperture defining a longitudinal slot having a plurality of wider sections spaced apart by narrower sections relative to the wider sections;

wherein the adjustment aperture is adapted to receive a post carried by the first paddle assembly, the first strut is arranged to be inserted through a paddle slot formed by the first paddle assembly formed and leading to an interior paddle channel, the plurality of wider sections configured to receive the post, and a plurality of narrower sections being too narrow for passage of the post therethrough;

wherein the lock mechanism includes a lever disposed along an inner paddle surface and extending parallel to the interior paddle channel of the first paddle assembly, the lever being coupled to the post which extends outward from the lever through the interior paddle channel to a post opening disposed on an outer paddle surface of the first paddle assembly, the lever biasing the post outward, such that the post traverses the interior paddle channel;

wherein the first paddle assembly defines first and second wings, spaced apart by a central portion including the post and the interior paddle channel, the first and second wings extending laterally relative to the central portion and a length of the first strut;

wherein the second wing defines a coupling member integrally formed with the first paddle assembly and arranged over an opening and proximate to a relief opening spaced apart from the opening.

2. The upright assembly of claim 1, wherein the first wing includes a first attachment member dividing first and second strap slots, and adapted to support a strap.

3. The upright assembly of claim 1, wherein the first and second wings define apertures along the first and second sides of and adjacent to the central portion.

4. The upright assembly of claim 1, wherein the central portion is arranged to secure to the first strut.

5. The upright assembly of claim 1, wherein a reinforcement is defined on an opposed side of the relief opening, and is formed by a localized thickened area of the second wing.

6. The upright assembly of claim 1, wherein the relief opening defines an arcuate shape and extends toward and about at least a portion of the coupling member.

7. The upright assembly of claim 1, wherein indicia is provided proximate the coupling member.

8. The upright assembly of claim 1, wherein the central portion extends beyond the first and second wings, the post is defined at an end portion of the central portion directed toward the hinge.

9. The upright assembly of claim 1, further comprising a second paddle assembly fixedly secured to the first strut at a location closer to the hinge than the first paddle assembly.

10. The upright assembly of claim 9, wherein the second paddle assembly defines a central portion having a height relative to a length of the first strut that is less than first and second heights of first and second wings, respectively, extending laterally from the central portion.

11. The upright assembly of claim 10, wherein the central portion of the second paddle assembly defines upper and lower recesses in longitudinal directions relative to a length of the first strut and relative to lateral directions from which the first and second wings extend relative to the first strut.

12. The upright assembly of claim 10, wherein the first and second wings are symmetrical in profile relative to one another.

13. The upright assembly of claim 10, wherein the first and second wings extend downwardly relative to the central portion and a length of the first strut more than upwardly relative to the central portion.

14. The upright assembly of claim 10 wherein the first and second wings have tapering heights extending toward lateral ends thereof extending away and remote from the central portion, the tapering heights being greater than a maximum height of the central portion.

15. The upright assembly of claim 9, wherein the second paddle assembly is only secured to the first strut within a central portion of the second paddle assembly, the second paddle assembly defining first and second wings extending laterally from the central portion and flexibly extending relative thereto, the first and second wings being adapted to receive first and second ends of a strap, respectively.

16. The upright assembly of claim 15, wherein the first wing defines at least one slot adapted to receive a first end of a strap, and the coupling member is adapted to receive a second end of the strap.

17. An upright assembly for an orthopedic device, the upright assembly comprising at least a first strut connected to a second strut by a hinge, wherein the upright assembly further comprises:
   a first paddle assembly having a lock mechanism, the first paddle assembly adapted to slide along the first strut and adjustably lock to the first strut among a plurality of predetermined locations by the lock mechanism, the first strut forming an adjustment aperture defining a longitudinal slot having a plurality of wider sections spaced apart by narrower sections relative to the wider sections;
   wherein the adjustment aperture is adapted to receive a post carried by the first paddle assembly, the first strut is arranged to be inserted through a paddle slot formed by the first paddle assembly formed and leading to an interior paddle channel, the plurality of wider sections configured to receive the post, and a plurality of narrower sections being too narrow for passage of the post therethrough;
   wherein the lock mechanism includes a lever disposed along an inner paddle surface and extending parallel to the interior paddle channel of the first paddle assembly, the lever being coupled to the post which extends outward from the lever through the interior paddle channel to a post opening disposed on an outer paddle surface of the first paddle assembly, the lever biasing the post outward, such that the post traverses the interior paddle channel;
   wherein the first paddle assembly defines first and second wings, spaced apart by a central portion including the post and the interior paddle channel, the first and second wings extending laterally relative to the central portion and a length of the first strut
   wherein the central portion extends beyond the first and second wings, the post is defined at an end portion of the central portion directed toward the hinge;
   a second paddle assembly fixedly secured to the first strut at a location closer to the hinge than the first paddle assembly;
   wherein the second paddle assembly defines a central portion having a height relative to a length of the first strut that is less than first and second heights of the first and second wings of the second paddle assembly, respectively;
   wherein the first and second wings are symmetrical in profile relative to one another;
   a first strap having first and second end portions arranged to secure to the first and second wings of the first paddle assembly, respectively;
   a second strap having first and second end portions arranged to secure to the first and second wings of the second paddle assembly, respectively;
   wherein the second wing of the first paddle assembly defines a coupling member integrally formed with the first paddle assembly and arranged over an opening and proximate to a relief opening spaced apart from the opening.

18. An orthopedic device, comprising:
   a first upright assembly having at least a first strut connected to a second strut by a hinge, wherein the first upright assembly further comprises:
   a first paddle assembly having a lock mechanism, the first paddle assembly adapted to slide along the first strut and adjustably lock to the first strut among a plurality of predetermined locations by the lock mechanism, the first strut forming an adjustment aperture defining a longitudinal slot having a plurality of wider sections spaced apart by narrower sections relative to the wider sections;
   wherein the adjustment aperture is adapted to receive a post carried by the first paddle assembly, the first strut is arranged to be inserted through a paddle slot formed by the first paddle assembly formed and leading to an interior paddle channel, the plurality of wider sections configured to receive the post, and a plurality of narrower sections being too narrow for passage of the post therethrough;
   wherein the lock mechanism includes a lever disposed along an inner paddle surface and extending parallel to the interior paddle channel of the first paddle assembly, the lever being coupled to the post which extends outward from the lever through the interior paddle channel to a post opening disposed on the outer paddle surface, the lever biasing the post outward, such that the post traverses the interior paddle channel;
   wherein the first paddle assembly defines first and second wings, spaced apart by a central portion including the post and the interior paddle channel, the first and second wings extending laterally relative to the central portion and the first strut;

wherein the central portion extends beyond the first and second wings, the post is defined at an end portion of the central portion directed toward the hinge;

a second paddle assembly fixedly secured to the first strut at a location closer to the hinge than the first paddle assembly;

wherein the second paddle assembly defines a central portion having a height relative to a length of the first strut that is less than first and second heights of first and second wings of the second paddle assembly, respectively;

wherein the first and second wings are symmetrical in profile relative to one another;

a first strap having first and second end portions arranged to secure to the first and second wings of the first paddle assembly, respectively;

a second strap having first and second end portions arranged to secure to the first and second wings of the second paddle assembly, respectively;

a second upright assembly having at least a third strut connected to a fourth strut by a second hinge, wherein the second upright assembly is connected to the first upright assembly by the first and second straps which engage a first paddle assembly and a second paddle assembly, respectively, of the second upright assembly;

wherein the second wing of the first paddle assembly defines a coupling member integrally formed with the first paddle assembly and arranged over an opening and proximate to a relief opening spaced apart from the opening.

* * * * *